United States Patent
Cavallo et al.

(10) Patent No.: US 10,688,196 B2
(45) Date of Patent: Jun. 23, 2020

(54) CROSS-LINKING AGENTS OF COLLAGEN FIBERS FOR THE USE IN THE TREATMENT OF CORNEAL ECTASIA

(71) Applicant: SOOFT ITALIA SPA, Montegiorgio (IT)

(72) Inventors: Giovanni Cavallo, Rome (IT); Edoardo Stagni, Catania (IT); Marco Biondi, Porto San Giorgio (IT); Piero Biondi, Porto San Giorgio (IT)

(73) Assignee: SOOFT ITALIA SPA, Montegiorgio (IT)

( * ) Notice: Subject to any disclaimer, the term of this patent is extended or adjusted under 35 U.S.C. 154(b) by 0 days.

(21) Appl. No.: 15/570,016

(22) PCT Filed: Apr. 29, 2015

(86) PCT No.: PCT/IT2015/000117
§ 371 (c)(1),
(2) Date: Oct. 27, 2017

(87) PCT Pub. No.: WO2016/174688
PCT Pub. Date: Nov. 3, 2016

(65) Prior Publication Data
US 2018/0236100 A1   Aug. 23, 2018

(51) Int. Cl.
| A61K 47/69 | (2017.01) |
| A61K 47/18 | (2017.01) |
| A61K 31/525 | (2006.01) |
| A61K 41/00 | (2020.01) |
| A61K 9/00 | (2006.01) |
| A61K 9/06 | (2006.01) |

(52) U.S. Cl.
CPC ........ *A61K 47/6951* (2017.08); *A61K 9/0048* (2013.01); *A61K 9/06* (2013.01); *A61K 31/525* (2013.01); *A61K 41/0057* (2013.01); *A61K 47/18* (2013.01); *A61K 47/183* (2013.01)

(58) Field of Classification Search
CPC ............ A61K 47/6951; A61K 41/0057; A61K 9/0048; A61K 31/525; A61K 47/18; A61K 9/06; A61K 47/183
USPC .......................................................... 514/58
See application file for complete search history.

(56) References Cited

U.S. PATENT DOCUMENTS

| 7,331,350 B2 | 2/2008 | Kochevar et al. |
| 2008/0015660 A1 | 1/2008 | Herekar |
| 2011/0152219 A1* | 6/2011 | Stagni ............ A61K 9/0048 514/81 |

FOREIGN PATENT DOCUMENTS

| EP | 2253321 A1 | 11/2010 |
| EP | 3288488 A1 | 3/2018 |
| EP | 3288588 B1 | 8/2018 |
| WO | 2004058289 A1 | 7/2004 |
| WO | 2009001396 A1 | 12/2008 |
| WO | 2009073600 A1 | 6/2009 |
| WO | 2010023705 A1 | 3/2010 |

OTHER PUBLICATIONS

Stojanovic et al. Safety and Efficacy of Epithelium-On Corneal Collagen Cross-Linking Using aMultifactorial Approach to Achieve Proper Stromal Riboflavin Saturation. Journal of Ophthalmology vol. 2012, p. 1-8, 2012. doi:10.1155/2012/498435 (Year: 2012).*
Rapp et al. Separate Mechanisms for Retinal Damage by Ultraviolet-A and Mid-Visible Light. Invest Ophthalmol Vis Sci 31:1186-1190, 1990. (Year: 1990).*
Ahmad I. et al., Int. J. Pharm. 2004. 280; 199-208.
Schuman Jorns M., et al., Eur. J. Biochem. 1975, 57, 35-48.
Ahmad I. et al., J. Photochem. Photobiol., B: Biol. 2008, 93, 82-87.
Yoshioka, S.; Stella, V., J. Stability of Drugs and Dosage Forms; Kluwer Academic/Plenum Publishers: New York, USA, 2000; pp. 97-99.
Moore W. W., Ireton R. C., Photochem. Photobiol. 1977, 25, 347-356.
Koziol J., Photochem. Photobiol. 1966, 5, 55-62.
Asker A. F., Habib M., J. Drug Dev. Ind. Pharm. 1990, 16, 149-156.
Holmström B., Oster G., J. Am. Chem. Soc. 1961, 83, 1867-1871.
Guttman D. E., J. Pharm. Sci. 1962, 51, 1162-1166.
Sato Y. et al., Chem. Pharm. Bull. 1982, 30, 1803-1810.
Loukas, Y. L., J. Pharm. Biomed. Anal. 2001, 26, 255-263.
De Jesus M. B. et al., E J. Pharm. Pharmacol. 2012, 64, 832-842.
Challa R. et al., AAPS PharmSciTech. 2005, 6, 329-357.
Grove C. et al., J. Cosmet. Sci. 2003, 54, 537-550.
Sultana Y. et al., Curr. Drug Delivery. 2006, 3, 207-217.
Roy D.K. et al., Spectrochim. Acta. 2009,73,201-204.
Terekhova I. V. et al., J. Inclusion Phenom. Macrocyclic Chem. 2011, 69, 167-172.
Morrison W. J. et al., Molecular pharmaceutics 2013, 10, 756-762.
Zaidi T. et al., Invest. Ophthalmol. Vis. Sci. 2008, 49, 1000-1009.
Ohtani Y. et al., Eur. J. Biochem. 1989, 186, 17-22.
Wollensak Gregor et al., "Collagen cross-linking of human and porcine sclera", Journal cataract and refractive surgery, 2004, vol. 30, pp. 689-69.
Spoerl E et al., "Techniques for stiffening the cornea", J. Refract Surg. 1999, 15: 711-713.
Wollensak Gregor., Curr Opin Ophthalmol. Aug. 2006;17(4):356-60.

* cited by examiner

*Primary Examiner* — Yih-Horng Shiao
(74) *Attorney, Agent, or Firm* — Flener IP & Business Law; Zareefa B. Flener

(57) ABSTRACT

It is described a complex of riboflavin into hydroxypropylated β-cyclodextrins as photosensitizer in the riboflavin-UV mediated cross-linking of corneal collage fibers and the relative ophthalmic compositions comprising it.

9 Claims, 5 Drawing Sheets

CROSS-LINKING AGENTS OF COLLAGEN FIBERS FOR THE USE IN THE TREATMENT OF CORNEAL ECTASIA

CROSS-REFERENCE TO RELATED APPLICATIONS

This application is a National Phase application of International Application No. PCT/IT2015/000117, filed on Apr. 29, 2015, the contents of which are hereby incorporated by reference.

FIELD OF THE INVENTION

The present invention relates to the medical pharmaceutical field and, more specifically, the technical field of topical ophthalmic compositions to be administered to perform the cross-linking (CXL) of corneal collagen useful in the treatment of keratoconus, namely an improved formulation of an ophthalmic composition containing riboflavin included into cyclodextrins enabling a better penetration in the corneal stroma compared to the prior art compositions.

In particular, riboflavin is included into hydroxypropil-β-cyclodextrins (HP-β-CD).

BACKGROUND OF THE INVENTION

The cornea is a convex transparent barrier that serves to maintain the intact structure of the eye and focus light onto the retina. The cornea derives its structural strength, shape and integrity from corneal collagen. The strength of the intertwined collagen strands is due to covalent cross-links established between and within collagen strands and between collagen and glycoproteins in the matrix. In physiologically robust structure of corneas, the enzyme lysyl oxidase performs the collagen cross-linking in a process called oxidative deamination using molecular oxygen present in the tissue. However, the biomechanical strength of corneal collagen can be reduced by a number of conditions including iatrogenic effect from surgical intervention, prosthesis, or medications, often the cause of corneal weakness can be congenital, idiopathic or due to microbial causes or trauma. In case of corneal weakness, interventional strategies to re-establish, or to improve, the strength of the corneal collagen fibers have to be applied and exploited.

Strengthening the weakened corneal collagen can be performed by chemical, physical and photochemical means. Chemical means such as glutaraldehyde, formaldehyde, glyceraldehyde, ribose, glucose and beta-nitro aliphatic alcohols introduced into the cornea have been investigated. Most methods using such chemical cross-linking agents have been abandoned due to concerns with toxicity and efficacy. Physical methods of strengthening corneal collagen include dehydrothermal treatment (desiccation of water from collagen), thermal heating and UVC or gamma radiation. However, many of these techniques have shown drawbacks including collagen denaturation and degradation of, damaging or killing keratocytes, and potentially toxic side effects.

The most promising method to cross-link compromised corneal collagen is photochemical cross-linking, which has been employed in human clinical use for the treatment of keratoconus and ectasia for some time. This method uses a photosensitizer, usually riboflavin monophosphate, and UVA light to create singlet oxygen in stromal collagen. The singlet oxygen reacts to convert lysine side-chains of collagen fibrils to allysine residues that spontaneously condense to cross link the collagen fibrils. Essentially this mimics the reaction caused by the natural enzyme lysyl oxidase. Photochemical cross-linking of the cornea has been demonstrated to successfully stop and reverse the progression of compromised collagen in keratoconus and ectasia and thousands of patients have received this treatment with few serious adverse events.

Photochemical treatment, sometimes called photodynamic therapy, is affected by three elements 1) excitation light, 2) photosensitizer molecules and 3) molecular oxygen. The goal of the chemical reaction is to produce singlet oxygen and the amount of each of the three variables of the reaction (light, photosensitizer, oxygen) determines the rate and amount of singlet oxygen produced. During the reaction, the molecular oxygen in the tissue is depleted. Available molecular oxygen in the tissue has often been the most limiting aspect of photochemical and photodynamic therapy. When tissue oxygen content is too low, the photochemical reaction produces little singlet oxygen. Instead, the reaction converts water into hydrogen peroxide that is cytotoxic and can stimulate the wound healing response with negative consequences. When the tissue oxygen content is relatively high, the photochemical reaction produces singlet oxygen at a rate approaching 100:1 singlet oxygen over hydrogen peroxide. Therefore, maintaining the molecular oxygen level high is a critical aspect of photochemical cross-linking. A rapid ROS production is important as the amount of oxygen decreases with the progress of time. When the solution warms the oxygen concentration is expected to lower as the oxygen solubility decreases with increasing temperature.

The wavelength of the excitation light determines the absorption features of the photosensitizer. The depth of penetration of the UVA light into the cornea is a function of the absorbance of the photosensitizer at various wavelengths and the concentration and distribution of photosensitizer molecules. This depth of penetration is a critical value in corneal cross-linking because too little penetration gives shallow, perhaps insufficient cross-linking, and too much penetration may injure the endothelium.

For riboflavin the maximum absorbance occurs in the UV light spectrum at around 365 nm and 445 nm. At these wavelengths excitation light is absorbed quickly and penetrates to the least depth into the tissue. The normal cornea is nominally around 500 microns in depth, and a layer of endothelial cells defines the back of the cornea.

Furthermore, the dynamics of the procedure for light penetration and the conversion of molecular oxygen to singlet oxygen depend upon the concentration of the photosensitizer in the tissue and the concentration of oxygen in the tissue.

There are several cautions to be observed when using UVA light and riboflavin for corneal cross-linking.

Firstly, UVA light can have cytotoxic effects on all living cells, and in particular, the corneal endothelial cells on the posterior layer of the cornea can be destroyed by excess UVA light or reactive oxygen species (ROS).

Then, activated riboflavin can produce cytotoxic hydrogen peroxide if oxygen molecules are not available. Such cytotoxic hydrogen peroxide can kill or disable healthy cells. The hydrogen peroxide also acts as a potent chemical messenger to other cells to initiate wound healing responses. These wound healing responses in the cornea may lead to edema, inflammation and differentiation of keratocytes into myofibroblasts with the production of types of collagen not conducive to optically transparent. In fact, corneal haze and scarring can result from myofibroblast formation.

Hence, a quicker reaction assures a less toxic event, and consequently, a better and more efficient action mechanism.

Corneal de-epithelialization is performed to promote riboflavin infusion into the stroma of the eye. The de-epithelialization procedure is intended to ensure that sufficient riboflavin phosphate is introduced into the eye to prevent excessive UVA radiation to the endothelium. In this case, the riboflavin concentration acts as a UVA sunscreen for the deeper endothelium. Additional adverse events may include postoperative infection/ulcer and stromal haze. Some patients report significant discomfort, pain and worse vision lasting roughly a week, and significantly worse vision than prior to the cross-linking procedure lasting for several months. Most of the adverse side effects are a result of the surgical removal of the corneal epithelium prior to the introduction of the riboflavin. The ability to predict the clinical outcome, i.e. the improvement of a patient's best-corrected visual acuity (BCVA) or prevention of reduction of BCVA over the long term, is not high.

In the prior art several alternative compounds to be used for corneal cross-linking in the treatment of keratoconus have been described.

The international patent application WO 2004/058289 discloses ophthalmic compositions comprising EDTA, EDTA sodium, EDTA potassium salt for treating ocular conditions of the cornea such as keratoconus.

Wollensak Gregor et al. in "Collagen cross-linking of human and porcine sclera", Journal cataract and refractive surgery, 2004, vol. 30, pages 689-695, discloses the process of cross-linking of sclera with glyceraldehyde, glutaraldehyde or riboflavin.

Spoerl E et al. in "Techniques for stiffening the cornea", J. Refract Surg. 1999, 15: 711-713, discloses corneal cross-linking performed with photosensitizers, such as riboflavin, and chemical cross-linkers, such as glutaraldehyde and Karnovsky's solution.

The application of a photosensitizer such as riboflavin-5-phosphate to a tissue, e.g. cornea, skin, tendon, cartilage, or bone, followed by photoactivation is described in U.S. Pat. No. 7,331,350, producing a tissue-tissue seal to repair a wound or to seal a tissue transplant. Said described method can be applied to different type of surgical procedures such as corneal transplant surgery, cataract surgery, laser surgery, keratoplasty, penetrating keratoplasty, refractive surgery, cornea reshaping.

Patent application US 2008/0015660 describes a method for performing oculoplasty for the treatment of corneal dystrophies/keratoconics including applying a riboflavin solution as photosensitizer to a human eye surface and irradiating the treatment region with controlled photoactivating radiation.

An ocular solution containing approximately 0.05-0.25% w/w of riboflavin phosphate and approximately 20% w/w of dextran for the use in the corneal cross-linking technique for the treatment of keratoconus is the object of the international patent application WO 2009/001396. The innovative contribution of the dextran to this solution is guaranteeing a good muco-adhesiveness to the ocular surface enabling a better performance of the contact and hence of the impregnation of the corneal stroma by the riboflavin solution.

A very simple formulation relating to a collyrium for the treatment of patients suffering from conical cornea has been recently disclosed by the European patent application EP 2 253 321. In such formulation, only containing riboflavin-5-phosphate, sodium chloride, benzal chloride and sterile water, the riboflavin-5-phosphate and the benzal chloride, acting as surface-active agent, assist the penetration of the collyrium in the corneal epithelium; compared to standard collyria for the treatment of conical cornea, the product obtained by this described composition has the advantage of not requiring the removal of the corneal epithelium.

A similar technical solution is obtained through UV-A irradiation of a riboflavin/collagen mixture in the presence of copious oxygen causing rapid cross-linking resulting in adhesion of the mixture in situ effecting its adhesion to underlying ocular structure. Such corneal and sclera tissue seal is disclosed in the International Patent Application WO 2009/073600 in order to obtain a structural augmentation of ocular tissue for better stabilizing progressive corneal diseases.

To overcome the problem of removing the corneal epithelium (de-epithelization), in order to facilitate the riboflavin absorption and the complete imbibition of the corneal stroma before starting the irradiation with UV-A which can create, albeit rarely, complications at a corneal level, pain, in addition to render the task of the oculist more difficult, the international patent application PCT/IT2009/000392, discloses the use of EDTA associated to tromethamine, and/or one or more photoenhancers chosen among: acridine yellow, quinidine yellow, methylene blue, erithrosine, either alone or mixed together, with riboflavin phosphate, for the preparation of ophthalmic compositions for the method of corneal cross-linking in the treatment of the keratoconus or of other ectasic disorders in order to favour the passage of the ophthalmic composition to the stroma through the corneal epithelium. The invention solves the technical problem of the poor capacity of riboflavin for diffusing through the epithelium and hence reaching the corneal stroma. In fact, by the addition of the disclosed association of EDTA and tromethamine, and/or one or more disclosed photoenhancers, the riboflavin phosphate based compound facilitates epithelial absorption associated to corneal CXL, avoiding the resort to the removal of the corneal epithelium, enabling a non-invasive corneal elimination or reduction of the anaesthesia and consequent fast healing without pain or possible complication for the patients.

However, despite the important advances in the relevant field of riboflavin solutions, there is still the need of more efficient ophthalmic compositions released to imbibe corneal stroma in the practice of corneal cross-linking for the treatment of keratoconus.

Therefore, it would be desirable to further improve the absorption of riboflavin, to reduce riboflavin administration time, without requiring the removal of the corneal epithelium, hence obtaining a noninvasive corneal cross-linking with elimination or reduction of the anesthesia, which does not need particular post treatment therapy, no edema due to the removal of the epithelium, and consequent fast healing without pain or possible complications for the patient.

Therefore, the need of alternative formulations of riboflavin composition to be used in corneal cross-linking is strongly felt.

So far, the most and more efficient corneal cross-linking agents employ riboflavin phosphate, that is a polar, negative charged molecule. Such feature does not allow to easily permeate the ocular membranes. A better approach, or at least an improvement of the present state of art, would use riboflavin, that is a lipophilic molecule, much better permeating the ocular membranes, however, the use of such molecule is very tough because this molecule is insoluble in water.

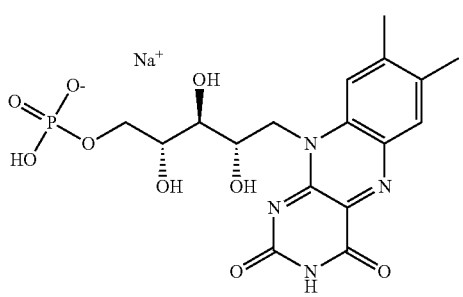 [SMILES: Cc1cc2nc3c(=O)[nH]c(=O)nc-3n(C[C@H](O)[C@H](O)[C@H](O)COP(=O)([O-])O)c2cc1C ; [Na+]]

Riboflavin-5-Phosphate Sodium

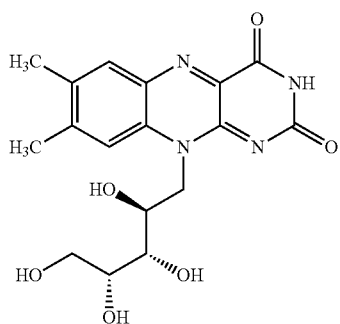 [SMILES: Cc1cc2nc3c(=O)[nH]c(=O)nc-3n(C[C@H](O)[C@H](O)[C@H](O)CO)c2cc1C]

Riboflavin

The photochemical cross-linking induced by riboflavin phosphate and UV-A inducing the photopolymerization of stromal collagen fibrils increasing its rigidity and resistance to progressive keratoectasia of keratoconus is still the more promising technique to cross-link compromised corneal collagen.

Corneal collagen Crosslinking (CXL) is performed with ultraviolet-A (UVA) irradiation at 370 nm and the photosensitizer riboflavin phosphate (vitamin B2). According to Wollensak (Wollensak, 2006), the photosensitizer is excited into its triplet state generating reactive oxygen species (ROS), which are mainly singlet oxygen and to a much lesser degree superoxide anion radicals. ROS can react further with various molecules inducing chemical covalent bonds forming bridges between amino groups of collagen fibrils (type II photochemical reaction). The biomechanical effect occurs immediately after irradiation leading to about 300% increase of the biomechanical rigidity of the cornea. The optimal wavelength of the ultraviolet (UV) radiation wherein riboflavin and riboflavin phosphate present maximal absorption is 370 nm.

Due to the peculiar chemical and physical properties of riboflavin molecule, both stability and degradation are the most concerned issue in the field of drug development and preparation based on riboflavin.

Riboflavin and riboflavin phosphate are very sensitive to light and high temperature, and therefore, these factors have to be carefully considered to guarantee its stability and the activity in pharmaceutical preparations. Several factors affecting the riboflavin stability and its functionality have been identified. These factors include radiation source, radiation intensity and wavelength, pH, presence of oxygen, buffer concentration and ionic strength, solvent polarity and viscosity, and use of stabilizers and complexing agents.

Some attempts to stabilize and shield photosensitive molecules from photodegradation due to exposure to light have been done, for example by combining them with some light absorbing agents, i.e. liposomes and cyclodetrins, as proposed by Gregoriadis and Loukas in EP0762871.

However, the need to deliver a high insoluble molecule such as riboflavin, but more lipophilic than riboflavin phosphate, counteracts safeguarding its capacity to interact with light to produce ROS that form bridges between amino groups of collagen fibrils leading to an increase of the rigidity of the cornea.

Photodegradation

According to the mechanisms involved in the photochemical reactions of flavins, both excited singlet and excited triplet states of riboflavin are implicated in the photodegradation reactions [1].

The photochemical reactions involved in the degradation of riboflavin are affected by a number of factors, such as radiation source, intensity and wavelengths. In fact, the emission features of the radiation source are an important factor that plays a significant role in the riboflavin photodegradation. In the dark, riboflavin is stable and remains unchanged under specified conditions for prolonged periods of time. In the dry form, riboflavin is not much affected by light while in the solution form it is rapidly degraded to various photoproducts through a variety of reactions under aerobic and anaerobic conditions.

The photodegradation of riboflavin is greatly affected by the pH of the medium and the photoproducts thus obtained are also dependent on pH. Hence, the pH of the solution has a significant effect on the photostability of riboflavin. Under acidic and neutral pH conditions, riboflavin is photodegraded to lumichrome, whereas in alkaline media it forms lumichrome along with lumiflavin.

It was also observed that the rate of photolysis of riboflavin is slowest in the pH range of 5-6 and is then increased tremendously (about 80 folds) in the alkaline region reaching a maximum at pH 10. This is probably due to the higher reactivity of the flavin triplet in this region [2].

The non-ionized forms of riboflavin are more susceptible to photodegradation as compared to the ionized forms and the optimum pH range for maintaining the vitamin preparations is 5-6.

Also buffers concentration and ionic strength play an important role in the photodegradation of riboflavin in aqueous solution. Different studies have shown the catalytic effect of buffer species including phosphate, sulfate, acetate and carbonate on the riboflavin solutions [3], while borate and citrate produce a stabilizing effect [4]. Solutions containing divalent anions have the tendency to catalyze the photodegradation of drug substances by break down the activated complex [5].

Furthermore, the rate of riboflavin photolysis is affected by solvent polarity, which causes changes in the conformation of the ribityl side chain to undergo degradation [6-7]. The riboflavin photodegradation has been found to be more rapid in organic solvents as compared to aqueous solutions. This could be linked to the physical properties of the solvents such as polarity, dielectric constant, viscosity, etc.

In order to stabilize riboflavin from photodegradation stabilizers, quenchers and complexing agents have been used.

Among the stabilizers the greatest stabilizing effect has been observed by disodium ethylenediamine (EDTA) (96.2%), followed by thiourea (88.2%), methylparaben (86.4%), DL-methionine (76.3%), sodium thiosulfate (72.9%), ribonucleic acid (59.3%) and reduced glutathione (26.2%). When riboflavin solutions were exposed to a 40 W fluorescent light (Sylvania fluorescent lamp with an intensity maintained at 1350 foot-candles), the photostabilizing effect of these agents was found to be dependent on their concentration as an increase in the effect was noted with an increase in concentration. Similarly, the pH of the medium and the buffer species (e.g., phosphate buffer), have been found to influence the rate of riboflavin photodegradation in the presence and absence of EDTA [8].

On the light absorption riboflavin is promoted to the excited singlet state and then to the excited triplet state. These excited states eventually return to the ground state by emitting fluorescence, phosphorescence or heat. The falling back of these states to the ground state may be due to self-quenching of the riboflavin molecule (internal quencher) or its photoproducts. Often external quenchers are added to riboflavin preparations in order to alter the quantum yield of the photoreaction without quenching the fluorescence of riboflavin [9].

Using various complexing agents is another strategy to photostabilize riboflavin. Caffeine is known to form molecular complexes with riboflavin and thus slow down its rate of chemical [10] and photodegradation reactions [11].

Different types of cyclodextrins have been studied for complexation with riboflavin to achieve its stabilization [12-13].

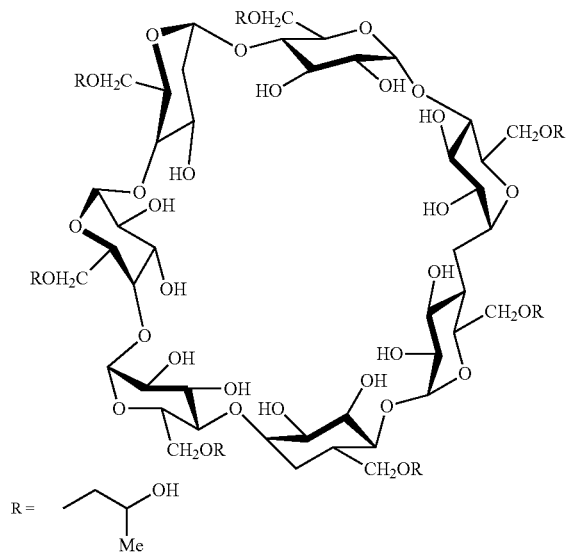

2-Hydroxypropyl-β-cyclodextrin

Cyclodextrins are toxoid-shaped oligosaccharides with hydrophilic external surfaces and a lipophilic internal cavity. They are able to form guest-host inclusion complexes with hydrophobic compounds increasing their solubility [14-15]. Studies have shown that pretreatment using cyclodextrin solutions can enhance corneal permeability of some drugs such as pilocarpine [16]. Sultana et al. reported their use in formulations containing corticosteroids, chloramphenicol, diclofenac and cyclosporine [17]. Roy et al. [18] and Terekhova et al. have demonstratedthat riboflavin can form complexes with cyclodextrins; however their studies were limited to the dynamics of complexation using α- and β-cyclodextrins.

The effects of various cyclodextrins on riboflavin solubility and permeability has been investigated through bovine cornea and described in Morris et al. 2013 [19]. It was found that α-cyclodextrin, and moreover β-cyclodextrin, increased riboflavin solubility, offering a significant enhancement in the aqueous solubility of riboflavin, but γ-cyclodextrin and hydroxypropyl-β-cyclodextrin failed to enhance drug solubility at any significant level, as compared with its solubility in water.

Size considerations and association constants seem to give reasonable explanation for the superior performance of β-cyclodextrin in solubilization of riboflavin.

The cavity of cyclodextrin determines which molecules are able to form inclusion complexes. When the cavity is small, as with α-cyclodextrin (4.7-5.3 Å), many drug molecules result too large to fit and are not able to form inclusion complexes: When the cavity is too large, drug molecules may be bound too loosely [14]. β-cyclodextrin is suitable for many pharmaceutical applications, with a cavity size of 6.0-6.5 Å, that can accommodate a wide range of drugs.

On the other hand, the size of riboflavin molecule was found to be 10×12 Å, which is too large to completely fit in any cyclodextrin cavity; however, the aromatic ring with attached methyl groups would suitably accommodate within β-cyclodextrin cavity and bind through weak hydrophobic affinity. The cavity of α-cyclodextrin would be too small to accommodate the aromatic ring of riboflavin, although partial complexation via the methyl groups could occur. According to this model the involvement of other parts of the riboflavin molecule, such as ribitol chain and pyrimidine ring, would be unlikely to participate in the formation of an inclusion complex. In the case of γ-cyclodextrin the fit would be too loose.

Corneal Permeability of Riboflavin

Morris et al. investigated the effect of cyclodextrins on permeability of riboflavin through fresh bovine corneas. The study has revealed that riboflavin permeability through bovine cornea was significantly enhanced using β-cyclodextrin solutions when compared to riboflavin in deionized water, but a, HP-β- and γ-cyclodextrin offered no significant improvement in drug permeation.

Microscopy analysis was conducted by Morris et al. in order to establish the effect of cyclodextrins on the integrity of fresh bovine cornea. All samples treated with α, β-, HP-β- and γ-cyclodextrins show a similar trend of increasing epithelial disruption, which becomes more noticeable with increasing exposure time to cyclodextrin solutions.

Furthermore, it can be supposed that such cyclodextrin-mediated increased permeation ability can be partially due, or promoted, by the cyclodextrin-mediated cholesterol extraction. In fact, cyclodextrins have previously been reported to extract cholesterol and other lipids from cell membranes. [20-21]. The extraction of cholesterol from bovine cornea by cyclodextrin solutions that had been in contact with biological tissue was confirmed by HPLC which has shown evidence of cholesterol extraction employing β-cyclodextrins and HP-β-cyclodextrins [19]. However, the result has shown that HP-β-cyclodextrins have a much lower ability in extracting cholesterol than β-cyclodextrins, so they have expected to have a lower diffusion capacity and ability to permeate the membranes eye.

Surprisingly, the Applicant has found that ophthalmic composition comprising riboflavin complexed in HP-β-cyclodextrins as photosensitizer, although made more stable by complexation, following irradiation, produces higher amount of superoxide anion than composition comprising riboflavin phosphate, currently used in corneal cross-linking procedure. Furthermore, although the lower ability in extracting cholesterol HP-β-cyclodextrins, the Applicant has unexpectedly found that HP-β-cyclodextrins complexes of riboflavin have an increased ability to permeate corneal stroma to perform collagen cross-linking.

SUMMARY

Hence, the right balance among solubility, photostability, photodegradation and permeation ability of riboflavin as photosensitizer to be employed in the cross-linking reaction is a crucial element to assure the best performance and result of the therapeutic treatment.

In particular, in order to achieve the best result, as the cross-linking agent reaches the ocular surface it has to be soluble and either stable and able to produce ROS, although such two technical features seem to counteract each other.

The purpose of the present invention is to provide improved cross-linking agents, based on riboflavin, to be administered in the practice of the treatment of keratoconus, or of other ectasic corneal diseases, having improved characteristics, considerably reducing the time required for the treatment and improving performance and therapeutic outcomes.

The object of the present invention is therefore to provide new formulations, useful for the treatment of corneal ectasia, based on riboflavin complexed in cyclodextrin solutions, characterized by a better transepithelial penetration in the corneal stroma and by an increased collagen structure rigidity if compared to the formulations of the state of the art.

DESCRIPTION OF THE INVENTION

Figure 1:
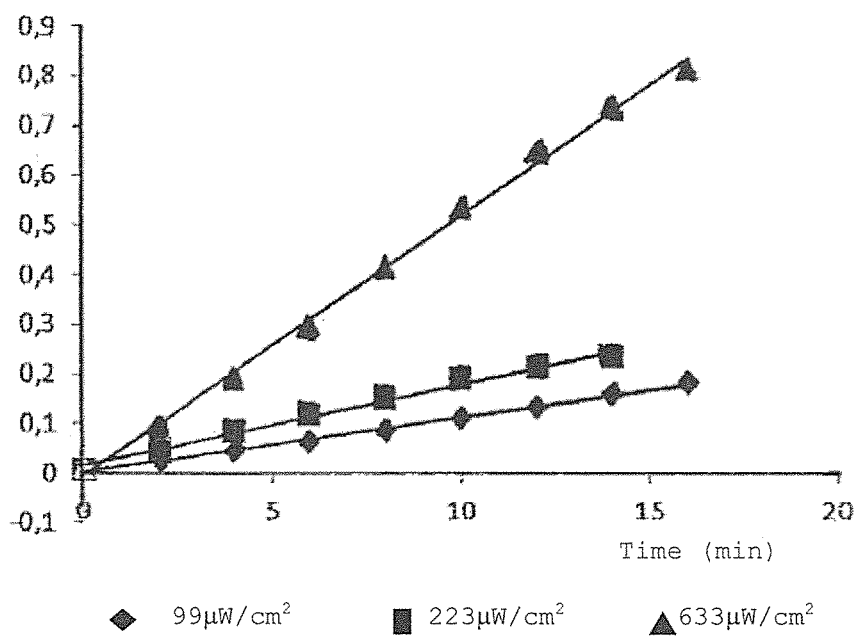
FIG. 1 is the graph showing the variation of the absorbance at 560 nm of the riboflavin phosphate+NTB sample when activated by different incident light intensity, respectively 99 μW/cm$^2$, 223 μW/cm$^2$, 633 μW/cm$^2$.

In one aspect the present invention provides improved photosensitizers to be used to perform the riboflavin-UV mediated cross-linking of corneal collagen fibers.

In a first embodiment of such aspect the photosensitizer is riboflavin included into cyclodextrins, in particular riboflavin is included into hydroxypropylated β-cyclodextrins (HP-β-CD).

Riboflavin sodium phosphate (molecular weight 456, negatively charged) is the preferred hydrophilic photosensitizing and photopolymerizing molecule mostly used in performing corneal cross-linking, however, its high solubility in water is linked to a poor capacity for diffusing through the epithelium and hence reaching the corneal stroma, instead riboflavin (molecular weight 376), lipophilic molecule with more diffusion capacity through the epithelium and hence reaching the corneal stroma, has a very poor solubility in water.

Cyclodextrins are water-soluble cyclic oligosaccharides consisting of six, seven, and eight α-(1-4)-linkedglucopyranose subunits, they are toroid-shaped molecules with hydrophilic external surfaces and a lipophilic internal cavity. They are able to form guest-host inclusion complexes with hydrophobic compounds rendering them more soluble.

Different kind of cyclodextrins are used in eye drop formulations to improve the aqueous solubility and corneal permeability of riboflavin. As above discussed it has been demonstrated that aqueous solution of β-cyclodextrin (10-30 mg/ml) can enhance the solubility of riboflavin, whereas the other oligosaccharides, even at higher concentration, are less effective, and that β-cyclodextrin enhances riboflavin permeability, while α-cyclodextrin, γ-cyclodextrin and hydroxypropyl-β-cyclodextrin offered no significant improvement in drug permeation.

Adversely to the literature, the Applicant provides evidence that the inclusion complex of riboflavin in hydroxypropyl-β-cyclodextrin improves corneas permeation ability of the riboflavin, producing thereby an inventive alternative as photosensitizer agent with respect to other riboflavin-cyclodextrin complexes and with respect to the currently used riboflavin phosphate which, as hydrophilic and negatively charged, is not easily absorbed by ocular membranes.

According to the invention the riboflavin complexed into hydroxypropylated β-cyclodextrins acts as phosensitizer to be used to perform the riboflavin-UV mediated cross-linking of corneal collagen fibers.

In another aspect the present invention provides improved ophthalmic formulations adapted to corneal imbibition associated to riboflavin and UV mediated cross-linking of corneal collagen fibers comprising riboflavin complexed into hydroxypropylated β-cyclodextrins.

The ophthalmic composition according to the invention further comprises EDTA H4 (Ethylene Diamine Tetraacetic Acid) and tromethamine. It is known from WO2010/023705 that the EDTA, or sodium EDTA, and tromethamine form together a ion-pair between the EDTA non salified carboxyl and the tromethamine which has a notable membrane penetrative capacity. The innovative and unexpected contribution proposed by the present invention, confirmed by experimental data in detail described below, is that the superoxide anion release determined by the use of the ophthalmic composition as photosensitizer is dependent on the amount of EDTA in the formulation. The amount of produced superoxide anion increases as in the formulation EDTA concentration increases.

According to the invention, the ophthalmic, composition suitably developed to perform corneal cross-linking comprising riboflavin included in cyclodextrins are more effective due to its ability to produce higher amount of superoxide anion than prior art formulation comprising riboflavin phosphate at equimolar ratio.

The presence of EDTA H4 notably enhances the ability to produce superoxide anion, and such effect is more marked in composition containing complexed riboflavin.

The ophthalmic composition according to the invention comprises:
  riboflavin/hydroxypropyl-β-cyclodextrin complex at concentration between 2 and 3% by weight, preferably between 2.5 and 2.9% by weight, more preferably 2.7% by weight;
  an amount of EDTA, or a salt thereof, in the range 0.05-0.25% by total weight, preferably EDTA, or its salt, is in the range 0.08-0.22% by total weight;
  an amount of tromethamine ranging from 0.12 to 0.3% by total weight, preferably from 0.134 to 0.285% by total weight.

In a particularly preferred embodiment the ophthalmic composition comprises EDTA H4 0.08-0.22% by total weight, even more preferably the amount of EDTA H4 is 0.1% of total weight of composition.

The presence of tromethamine assures also that formulation is appropriately buffered to manage the optimal pH value of the composition which is ranging between 6.0 and 7.3, preferably between 6.6 and 7.2.

It should be pointed out that the ophthalmic composition may be hypotonic, isotonic or even hypertonic due to the further and eventual addition of sufficient osmolite, such as salts or other suitable agents, to achieve the desired osmolarity value, depending on the system which the composition has to be applied to.

The ophthalmic composition according to the invention further comprises active principles, buffering agents, preservatives, vehicles, diluents, pharmaceutically acceptable excipients.

The ophthalmic compositions of the present invention can be prepared in the technical form of collyriums, eye-drops, eye-washes, ointments, and in any case in all the pharmaceutical technical forms that enable a corneal application according to known techniques.

The technical feature of the composition according to the invention allows improving performance of prior art composition overcoming the relative drawback due to phosphate anion of riboflavin. In fact, in the prior art ophthalmic compositions devoted to accomplish corneal cross-linking the use of phosphate riboflavin assure an acceptable level of the solubility of the riboflavin molecule, otherwise not soluble, but it is known that phosphate riboflavin itself adversely affects stability and photodegradation thereof, influencing the ROS production and pathway to the corneal cross linking. Hence, the use of a riboflavin complexed in cyclodextrins, and in particular in HP-β-cyclodextrins, maintaining a good level of solubility and an enhanced ability to produce ROS, can be an alternative and more efficient agent for the use in the therapeutic cross-linking procedure which allows to modify cross-linking parameters, modality and application time in order to achieve a better compliance for the patient.

Given hereinafter are examples provided by way of illustration, without this implying any limit to the present invention. Other aspects, advantages and modifications within the scope of the invention will be apparent to those skilled in the art to which the invention pertains.

Formulations are reported below; the dosage of the individual components is expressed in weight percentage.

| Formulation 1 | |
| --- | --- |
| Ingredients | % w/w |
| Riboflavin/HP-β-cyclodextrin complex | 2.7 |
| wherein: Riboflavin | 0.1 |
| HP-β-cyclodextrin | 2.6 |
| Tromethamine | 0.134 |
| EDTA H4 | 0.1 |
| Distilled water | Up to 100 g |
| pH | 6.6 |

| Formulation 2 | |
| --- | --- |
| Ingredients | % w/w |
| Riboflavin/HP-β-cyclodextrin complex | 2.7 |
| wherein: Riboflavin | 0.1 |
| HP-β-cyclodextrin | 2.6 |
| Tromethamine | 0.138 |
| EDTA H4 | 0.1 |
| Distilled water | Up to 100 g |
| pH | 6.8 |

| Formulation 3 | |
|---|---|
| Ingredients | % w/w |
| Riboflavin/HP-β-cyclodextrin complex | 2.7 |
| wherein: Riboflavin | 0.1 |
| HP-β-cyclodextrin | 2.6 |
| Tromethamine | 0.142 |
| EDTA H4 | 0.1 |
| Distilled water | Up to 100 g |
| pH | 7.0 |

| Formulation 4 | |
|---|---|
| Ingredients | % w/w |
| Riboflavin/HP-β-cyclodextrin complex | 2.7 |
| wherein: Riboflavin | 0.1 |
| HP-β-cyclodextrin | 2.6 |
| Tromethamine | 0.150 |
| EDTA H4 | 0.1 |
| Distilled water | Up to 100 g |
| pH | 7.2 |

| Formulation 5 | |
|---|---|
| Ingredients | % w/w |
| Riboflavin/HP-β-cyclodextrin complex | 2.7 |
| wherein: Riboflavin | 0.1 |
| HP-β-cyclodextrin | 2.6 |
| Tromethamine | 0.235 |
| EDTA H4 | 0.2 |
| Distilled water | Up to 100 g |
| pH | 6.6 |

| Formulation 6 | |
|---|---|
| Ingredients | % w/w |
| Riboflavin/HP-β-cyclodextrin complex | 2.7 |
| wherein: Riboflavin | 0.1 |
| HP-β-cyclodextrin | 2.6 |
| Tromethamine | 0.242 |
| EDTA H4 | 0.2 |
| Distilled water | Up to 100 g |
| pH | 6.8 |

| Formulation 7 | |
|---|---|
| Ingredients | % w/w |
| Riboflavin/HP-β-cyclodextrin complex | 2.7 |
| wherein: Riboflavin | 0.1 |
| HP-β-cyclodextrin | 2.6 |
| Tromethamine | 0.260 |
| EDTA H4 | 0.2 |
| Distilled water | Up to 100 g |
| pH | 7.0 |

| Formulation 8 | |
|---|---|
| Ingredients | % w/w |
| Riboflavin/HP-β-cyclodextrin complex | 2.7 |
| wherein: Riboflavin | 0.1 |
| HP-β-cyclodextrin | 2.6 |
| Tromethamine | 0.280 |
| EDTA H4 | 0.2 |
| Distilled water | Up to 100 g |
| pH | 7.2 |

The ophthalmic composition according to the invention are sterilized according to standard procedure known to skilled person, preferably by filtration or by heating at 121° C., 1 atm, for 10-15 minutes.

EXPERIMENTAL PART

Data from the experimental studies showing main advantages by using the riboflavin/HP-β-cyclodextrin complex and the ophthalmic composition comprising such inclusion complex to perform corneal cross-linking carried out by the Applicant are presented below. The experimental work was focused to:

1. to compare the stability of riboflavin/HP-β-cyclodextrin complex with respect to riboflavin phosphate at different pH values;
2. to determine and compare the ability of producing ROS of riboflavin in HP-β-cyclodextrin complex with respect to riboflavin phosphate;
3. to evaluate the ability of riboflavin/HP-β-cyclodextrin complex of permeating rabbit corneas ex vivo;
4. to compare the ability of riboflavin/HP-β-cyclodextrin complex, versus riboflavin/β-cyclodextrin complex in permeating rabbit corneas ex vivo.

STUDY 1—Comparison of the Stability of Riboflavin/HP-β-Cyclodextrin Complex with Respect to Riboflavin Phosphate at Different pH Values.

Preparation of the Inclusion Complex of Riboflavin and Control Solutions

For the inclusion of riboflavin in HP-β-cyclodextrin 100 mg of riboflavin were dissolved in 200 ml of distilled water by magnetic stirring overnight.

2.6 g of HP-β-cyclodextrin were added and dissolved at 70° C. by rotavapor for at least 8 hrs.

Mixing and heating in rotavapor was repeated twice more. A clear deep yellow color solution was obtained.

The composition of the complex riboflavin-HP-β cyclodextrin so obtained is given in the table below.

| Diluted composition | Amount in g | % w/v |
|---|---|---|
| Riboflavin | 0.100 | 0.05 |
| HP-β-cyclodextrin | 2.6 | 1.3 |
| Distilled water | 200 | |

The solution of riboflavin included into HP-β-cyclodextrin was freeze-dried and the obtained yellow product was utilized to manufacture collirium compositions according to formulations 1 to 8 as above described to be tested in the following described experiments. Such formulations were compared to control compositions having the same pH, comprising the same amount of EDTA H4 and tromethamine and wherein complexed riboflavin was replaced by riboflavin phosphate. The relative formulations are given below.

| Formulation 1C | |
|---|---|
| Ingredients | % w/w |
| Riboflavin phosphate | 0.126 |
| Tromethamine | 0.134 |
| EDTA H4 | 0.1 |
| Distilled water | Up to 100 g |
| pH | 6.6 |

| Formulation 2C | |
|---|---|
| Ingredients | % w/w |
| Riboflavin phosphate | 0.126 |
| Tromethamine | 0.138 |
| EDTA H4 | 0.1 |
| Distilled water | Up to 100 g |
| pH | 6.8 |

| Formulation 3C | |
|---|---|
| Ingredients | % w/w |
| Riboflavin phosphate | 0.126 |
| Tromethamine | 0.142 |
| EDTA H4 | 0.1 |
| Distilled water | Up to 100 g |
| pH | 7.0 |

| Formulation 4C | |
|---|---|
| Ingredients | % w/w |
| Riboflavin phosphate | 0.126 |
| Tromethamine | 0.150 |
| EDTA H4 | 0.1 |
| Distilled water | Up to 100 g |
| pH | 7.2 |

| Formulation 5C | |
|---|---|
| Ingredients | % w/w |
| Riboflavin phosphate | 0.126 |
| Tromethamine | 0.235 |
| EDTA H4 | 0.2 |
| Distilled water | Up to 100 g |
| pH | 6.6 |

| Formulation 6C | |
|---|---|
| Ingredients | % w/w |
| Riboflavin phosphate | 0.126 |
| Tromethamine | 0.242 |
| EDTA H4 | 0.2 |
| Distilled water | Up to 100 g |
| pH | 6.8 |

| Formulation 7C | |
|---|---|
| Ingredients | % w/w |
| Riboflavin phosphate | 0.126 |
| Tromethamine | 0.260 |
| EDTA H4 | 0.2 |
| Distilled water | Up to 100 g |
| pH | 7.0 |

| Formulation 8C | |
|---|---|
| Ingredients | % w/w |
| Riboflavin phosphate | 0.126 |
| Tromethamine | 0.280 |
| EDTA H4 | 0.2 |
| Distilled water | Up to 100 g |
| pH | 7.2 |

All riboflavin compositions, both complexed and control (1-8 and 1C-8C) were steam sterilized according to the standard method known to the skilled persons in the field (temperature: 121° C.; pressure: 1 atm; time: at least 20 minutes).

For the inclusion of riboflavin in β-cyclodextrin the same protocol as for the inclusion in HP-β-cyclodextrin was followed: 100 mg of riboflavin were dissolved in 200 ml of distilled water by magnetic stirring overnight. 2.6 g of β-cyclodextrin were added and dissolved at 70° C. by rotavapor for at least 8 hrs.

Mixing and heating in rotavapor was repeated twice more. A clear deep yellow color solution was obtained.

The composition of the complex riboflavin-β cyclodextrin so obtained is given in the table below.

| Diluted composition | Amount in g | % w/v |
|---|---|---|
| Riboflavin | 0.100 | 0.05 |
| β-cyclodextrin | 2.6 | 1.3 |
| Distilled water | 200 | |

The solution of riboflavin included into β-cyclodextrin was freeze-dried and the obtained yellow product was utilized to manufacture the ophthalmic compositions.

| Powder composition | Amount in g | % w/v |
|---|---|---|
| Riboflavin | 0.100 | 3.7 |
| β-cyclodextrin | 2.6 | 96.3 |
| Total weigh of the inclusion | 2.7 | |

The formulation of the ophthalmic compositions comprising the riboflavin-β cyclodextrin complex is given in the table below.

| Ingredients | % w/w | % |
|---|---|---|
| Riboflavin/β-cyclodextrin complex | 2.7 | |
| wherein: Riboflavin | 0.1 | 0.1 |
| β-cyclodextrin | 2.6 | 2.6 |
| Tromethamine | 0.134 | 0.134 |
| EDTA H4 | 0.1 | 0.1 |
| Distilled water | Up to 100 g | |

| Ingredients | % w/w | % |
|---|---|---|
| pH | | 6.8 |

The riboflavin/β-cyclodextrin complex in powder initially dissolve in the solution, but in about one hour time the product precipitates. This behavior is likely due to little solubility of β-cyclodextrin in water, or more precisely, to the minor solubility of β-cyclodextrin than HP-β-cyclodextrin. The complete solubilization of the complex riboflavin/β-cyclodextrin by diluting the product two fold up to obtain respectively a 0.050% final concentration of riboflavin and 1.2% final concentration of β-cyclodextrin confirms the hypothesis.

Below are reported the formulations and the main features of the two ophthalmic compositions comprising riboflavin/β-cyclodextrin complex that that in the experimental condition have shown a good stability.

| Ingredients | Amount in g | % w/w |
|---|---|---|
| Riboflavin/β-cyclodextrin complex | 2.7 | |
| wherein: Riboflavin | | 0.050 |
| β-cyclodextrin | | 1.30 |
| Tromethamine | 0.134 | 0.134 |
| EDTA H4 | 0.10 | 0.1 |
| Distilled water | Up to 100 g | |
| Osmolality | | 26 |
| pH before sterilization | | 7.4 |
| Steam sterilization 20 min., 1 atm, 121° C. | | |
| pH after sterilization | | 7.0 |

| Ingredients | Amount in g | % w/w |
|---|---|---|
| Riboflavin/β-cyclodextrin complex | 2.7 | 0.050 |
| wherein: Riboflavin | | 1.30 |
| β-cyclodextrin | | |
| Tromethamine | 0.268 | 0.268 |
| EDTA H4 | 0.20 | 0.20 |
| Distilled water | Up to 100 g | |
| Osmolality | | 35 |
| pH before sterilization | | 7.0 |
| Steam sterilization 20 min., 1 atm, 121° C. | | |
| pH after sterilization | | 7.0 |

Riboflavin Titer Determination

Riboflavin titer determination before and after sterilization was assessed according to standard method, results are shown in the tables below.

TABLE 1

Riboflavin titer in compositions 1-8 comprising inclusion complex of riboflavin and HP-β-cyclodextrin.

| Composition | Technical features | Sterilization | Riboflavin % by weight |
|---|---|---|---|
| 1 | Inclusion complex riboflavin and HP-β-cyclodextrin (0.1% p/p-2.6% p/p), 0.1% p/p EDTAH4, 0.134% Tris, pH 6.6 | 20 min, 1 atm, 121° C. | 89.0 |
| 2 | Inclusion complex riboflavin and HP-β-cyclodextrin (0.1% p/p-2.6% p/p), 0.1% p/p EDTAH4, 0.138% Tris, pH 6.8 | 20 min, 1 atm, 121° C. | 89.0 |
| 3 | Inclusion complex riboflavin and HP-β-cyclodextrin (0.1% p/p-2.6% p/p), 0.1% p/p EDTAH4, 0.142% Tris, pH 7.0 | 20 min, 1 atm, 121° C. | 91.9 |
| 4 | Inclusion complex riboflavin and HP-β-cyclodextrin (0.1% p/p-2.6% p/p), 0.1% p/p EDTAH4, 0.150% Tris, pH 7.2 | 20 min, 1 atm, 121° C. | 93.9 |
| 4 | Inclusion complex riboflavin and HP-β-cyclodextrin (0.1% p/p-2.6% p/p), 0.1% p/p EDTAH4, 0.150% Tris, pH 7.2 | no | 98.0 |
| 5 | Inclusion complex riboflavin and HP-β-cyclodextrin (0.1% p/p-2.6% p/p), 0.2% p/p EDTAH4, 0.235% Tris, pH 6.6 | 20 min, 1 atm, 121° C. | 96.0 |
| 6 | Inclusion complex riboflavin and HP-β-cyclodextrin (0.1% p/p-2.6% p/p), 0.2% p/p EDTAH4, 0.242% Tris, pH 6.8 | 20 min, 1 atm, 121° C. | 79.2 |
| 7 | Inclusion complex riboflavin and HP-β-cyclodextrin (0.1% p/p-2.6% p/p), 0.2% p/p EDTAH4, 0.260% Tris, pH 7.0 | 20 min, 1 atm, 121° C. | 78.6 |
| 8 | Inclusion complex riboflavin and HP-β-cyclodextrin (0.1% p/p-2.6% p/p), 0.2% p/p EDTAH4, 0.280% Tris, pH 7.2 | 20 min, 1 atm, 121° C. | 79.0 |
| 8 | Inclusion complex riboflavin and HP-β-cyclodextrin (0.1% p/p-2.6% p/p), 0.2% p/p EDTAH4, 0.280% Tris, pH 7.2 | no | 98.0 |

TABLE 2

Riboflavin titer in compositions 1C-8C comprising riboflavin phosphate in water solution

| Composition | Technical features | Sterilization | Riboflavin % by weight |
|---|---|---|---|
| 1C | Riboflavin phosphate 0.126% p/p, 0.1% p/p EDTAH4, 0.134% Tris, pH 6.6 | 20 min, 1 atm, 121° C. | 98.5 |
| 2C | Riboflavin phosphate 0.126% p/p, 0.1% p/p EDTAH4, 0.138% Tris, pH 6.8 | 20 min, 1 atm, 121° C. | 98.2 |
| 3C | Riboflavin phosphate 0.126% p/p, 0.1% p/p EDTAH4, 0.142% Tris, pH 7.0 | 20 min, 1 atm, 121° C. | 95.4 |
| 4C | Riboflavin phosphate 0.126% p/p, 0.1% p/p EDTAH4, 0.150% Tris, pH 7.2 | 20 min, 1 atm, 121° C. | 96.4 |
| 4C | Riboflavin phosphate 0.126% p/p, 0.1% p/p EDTAH4, 0.150% Tris, pH 7.2 | no | 100 |
| 5C | Riboflavin phosphate 0.126% p/p, 0.2% p/p EDTAH4, 0.235% Tris, pH 6.6 | 20 min, 1 atm, 121° C. | 96.1 |
| 6C | Riboflavin phosphate 0.126% p/p, 0.2% p/p EDTAH4, 0.242% Tris, pH 6.8 | 20 min, 1 atm, 121° C. | 100 |
| 7C | Riboflavin phosphate 0.126% p/p, 0.2% p/p EDTAH4, 0.260% Tris, pH 7.0 | 20 min, 1 atm, 121° C. | 96.5 |

TABLE 2-continued

Riboflavin titer in compositions 1C-8C comprising riboflavin phosphate in water solution

| Composition | Technical features | Sterilization | Riboflavin % by weight |
|---|---|---|---|
| 8C | Riboflavin phosphate 0.126% p/p, 0.2% p/p EDTAH4, 0.280% Tris, pH 7.2 | 20 min, 1 atm, 121° C. | 98.9 |
| 8C | Riboflavin phosphate 0.126% p/p, 0.2% p/p EDTAH4, 0.280% Tris, pH 7.2 | no | 98.5 |

The framework relative to the stability of riboflavin included in HP-β-cyclodextrin is completed by Table 3 where the data of the percentage of riboflavin after sterilization for prolonged times at 121° C. under different conditions are reported.

TABLE 3

Riboflavin stability in inclusion of HP-β-cyclodextrin under different conditions.

| Technical features | Sterilization | Riboflavin % by weight |
|---|---|---|
| In presence of EDTA H4-Tromethamine (0.1% w/w EDTAH4, 0.134% Tris) | | |
| Inclusion complex riboflavin and HP-β-cyclodextrin (0.1% p/p-2.6% p/p) | 20 min, 1 atm, 121° C. | 89.3 |
| Inclusion complex riboflavin and HP-β-cyclodextrin (0.1% p/p-2.6% p/p) | 30 min, 1 atm, 121° C. | 88.88 |
| Inclusion complex riboflavin and HP-β-cyclodextrin (0.1% p/p-2.6% p/p) | 45 min, 1 atm, 121° C. | 82.6 |
| In presence of EDTA H4 (0.1% p/p), Tris (0.05% p/p) and phosphate buffer (Na$_2$HPO$_4$ 0.150% p/p - NaH$_2$PO$_4$ 0.122% p/p) | | |
| Inclusion complex riboflavin and HP-β-cyclodextrin (0.1% p/p-2.6% p/p) | 20 min, 1 atm, 121° C. | 52.8 |
| Inclusion complex riboflavin and HP-β-cyclodextrin (0.1% p/p-2.6% p/p) | 30 min, 1 atm, 121° C. | 41.9 |
| Inclusion complex riboflavin and HP-β-cyclodextrin (0.1% p/p-2.6% p/p) | 45 min, 1 atm, 121° C. | 32.2 |
| In presence of phosphate buffer (Na$_2$HPO$_4$ 0.150% p/p - NaH$_2$PO$_4$ 0.122% p/p) | | |
| Inclusion complex riboflavin and HP-β-cyclodextrin (0.1% p/p-2.6% p/p) | 20 min, 1 atm, 121° C. | 56.6 |
| Inclusion complex riboflavin and HP-β-cyclodextrin (0.1% p/p-2.6% p/p) | 30 min, 1 atm, 121° C. | 46.5 |
| Inclusion complex riboflavin and HP-β-cyclodextrin (0.1% p/p-2.6% p/p) | 45 min, 1 atm, 121° C. | 35.4 |
| In presence of borate buffer (sodium tetraborate 1.40% p/p - boric acid 0.125% p/p) | | |
| Inclusion complex riboflavin and HP-β-cyclodextrin (0.1% p/p-2.6% p/p) | 20 min, 1 atm, 121° C. | 72.4 |
| In presence of distilled water | | |
| Inclusion complex riboflavin and HP-β-cyclodextrin (0.1% p/p-2.6% p/p) | 20 min, 1 atm, 121° C. | 99.1 |
| Inclusion complex riboflavin and HP-β-cyclodextrin (0.1% p/p-2.6% p/p) | 30 min, 1 atm, 121° C. | 97.8 |
| Inclusion complex riboflavin and HP-β-cyclodextrin (0.1% p/p-2.6% p/p) | 45 min, 1 atm, 121° C. | 96.6 |

The stability of riboflavin phosphate in control ophthalmic compositions for the use in the corneal cross-linking, after sterilization for prolonged times at 121° C. and under different conditions, is shown in Table 4

TABLE 4

Riboflavin phosphate stability under different conditions

| Technical features | Sterilization | Riboflavin % by weight |
|---|---|---|
| In presence of EDTA H4 (0.1% p/p), Tris (0.05% p/p) and phosphate buffer (Na$_2$H$_2$PO$_4$ 0.150% p/p - NaH$_2$PO$_4$ 0.122% p/p) | | |
| Riboflavin phosphate (0.1% p/p-2.6% p/p) | 20 min, 1 atm, 121° C. | 67.0 |
| Riboflavin phosphate (0.1% p/p-2.6% p/p) | 30 min, 1 atm, 121° C. | 60.0 |
| Riboflavin phosphate (0.1% p/p-2.6% p/p) | 45 min, 1 atm, 121° C. | 50.0 |
| In presence of phosphate buffer (Na$_2$HPO$_4$ 0.150% p/p - NaHPO$_4$ 0.122% p/p) | | |
| Riboflavin phosphate (0.1% p/p-2.6% p/p) | 20 min, 1 atm, 121° C. | 65.0 |
| Riboflavin phosphate (0.1% p/p-2.6% p/p) | 30 min, 1 atm, 121° C. | 40.0 |
| Riboflavin phosphate (0.1% p/p-2.6% p/p) | 45 min, 1 atm, 121° C. | 39.0 |
| In presence of borate buffer (sodium tetraborate 1.40% p/p - boric acid 0.125% p/p) | | |
| Riboflavin phosphate (0.1% p/p-2.6% p/p) | 20 min, 1 atm, 121° C. | 68.0 |
| In presence of distilled water | | |
| Riboflavin phosphate (0.1% p/p-2.6% p/p) | 20 min, 1 atm, 121° C. | 95.0 |
| Riboflavin phosphate (0.1% p/p-2.6% p/p) | 30 min, 1 atm, 121° C. | 92.0 |
| Riboflavin phosphate (0.1% p/p-2.6% p/p) | 45 min, 1 atm, 121° C. | 90.0 |

STUDY 2—Determination of the Ability to Produce ROS by Riboflavin Included in HP-β-Cyclodextrin.

The comparison of the ability of producing ROS by compositions comprising riboflavin phosphate and inclusion complex of riboflavin in HP-β-cyclodextrin was carried out by a method to measure oxygen radicals following reduction of Nitro Blue Tetrazolium (NTB) to Formazan Blue.

The rational of the method is based on the fact that some organic molecules, both natural and synthetic, when irradiated with a particular wavelength, activate and, by interacting with oxygen, produce superoxide anion. Namely, riboflavin molecule (photoactivator) irradiated at 366 nm reacts with oxygen, superoxide anion is produced which reduces NBT (detector) to Blue Formazan, resulting color variation from yellow to blue, blue color intensity is detected at 560 nm. As the amount of produced superoxide anion correlates with the amount of reduced NBT, from the absorption rate of reduced NBT is obtained the amount of ROS, thereby the ROS production can be expressed as function of irradiation time (minutes).

The ROS measurement is performed by a photoactivation chamber which enables to irradiate in controlled conditions the solutions of photoactivator and detector. The controlled parameters are emission specificity, uniform radiance, irradiation intensity, irradiation time.

Set Up of Experiment Conditions and Preparation of Control Compositions

Experiment control compositions were prepared as described below:

Photoactivator Stock Solution:

Riboflavin phosphate dihydrate stock solution

| Ingredients | % w/w |
| --- | --- |
| Riboflavin sodium 5'monophosphate dihydrate | 0.147 |
| $NaH_2PO_4 \cdot 2H_2O$ | 0.685 |
| $Na_2HPO_4 \cdot 2H_2O$ | 0.285 |
| Distilled water | Up to 100 g |
| pH | 7.2 |

Detector Stock Solution:

NBT stock solution

| Ingredients | |
| --- | --- |
| Nitro Blue Tetrazolium | 61.27 mg |
| Distilled water | 30 ml |

Riboflavine 5'-(Dihydrogen Phosphate), Monosodium Salt, Dehydrate Control Sample (Photoactivator):
Three milliliters of Riboflavin 5'-(dihydrogen phosphate), monosodium salt, stock solution were mixed to 1 ml of distilled water.

NBT Control Sample (Detector):
One milliliter of NBT stock solution was mixed to 3 ml of distilled water.

Reference Sample:
Three milliliters of riboflavin 5'-(dihydrogen phosphate), monosodium salt, stock solution (photoactivator) were mixed to 1 ml of NBT stock solution (detector).

Riboflavin-5'-(dihydrogen phosphate), monosodium salt, control sample, NBT control sample and reference sample were irradiated at different incident light intensity (99 $\mu W/cm^2$, 223 $\mu W/cm^2$, 633 $\mu W/cm^2$) (366 nm wavelength) in the photoactivation chamber, and absorbance at 560 nm is recorded. During the irradiation the temperature of the solutions was measured. At the end of the measurements the solution temperature resulted to have risen of 0.8° C. for higher incident irradiation light intensity. Therefore reasonably the effect of temperature is marginal on these absorbance measures.

The variation of absorbance at 560 nm for the three samples is reported in the following tables.

TABLE 5

Variation of absorbance of riboflavin-5'-(dihydrogen phosphate), monosodium salt, control sample

| Time min | Incident light intensity 99 $\mu W/cm^2$ Absorbance at 560 nm | Incident light intensity 223 $\mu W/cm^2$ Absorbance at 560 nm | Incident light intensity 633 $\mu W/cm^2$ Absorbance at 560 nm |
| --- | --- | --- | --- |
| 0 | 0.008 | 0.008 | 0.008 |
| 2 | 0.009 | 0.009 | 0.010 |
| 4 | 0.009 | 0.010 | 0.013 |
| 6 | 0.009 | 0.012 | 0.014 |
| 8 | 0.009 | 0.012 | 0.015 |
| 10 | 0.010 | 0.014 | 0.015 |
| 12 | 0.010 | 0.014 | 0.016 |
| 14 | 0.010 | 0.015 | 0.018 |
| 16 | 0.010 | 0.016 | 0.019 |

Results
The irradiation of the solution comprising only riboflavin phosphate causes no appreciable change of the absorption. This trend is confirmed at different light intensities

TABLE 6

Variation of absorbance of NBT control sample

| Time min | Incident light intensity 99 $\mu W/cm^2$ Absorbance at 560 nm | Incident light intensity 223 $\mu W/cm^2$ Absorbance at 560 nm | Incident light intensity 633 $\mu W/cm^2$ Absorbance at 560 nm |
| --- | --- | --- | --- |
| 0 | 0.002 | 0.002 | 0.002 |
| 2 | 0.002 | 0.002 | 0.002 |
| 4 | 0.002 | 0.002 | 0.003 |
| 6 | 0.002 | 0.002 | 0.003 |
| 8 | 0.002 | 0.003 | 0.004 |
| 10 | 0.002 | 0.003 | 0.004 |
| 12 | 0.002 | 0.003 | 0.005 |
| 14 | 0.002 | 0.003 | 0.005 |
| 16 | 0.002 | 0.004 | 0.005 |

Results
The irradiation of the solution comprising only NBT causes no appreciable change of the absorption. This trend is confirmed at different light intensities

TABLE 7

Variation of absorbance of reference sample (Riboflavin phosphate + NTB)

| Time min | Incident light intensity 99 $\mu W/cm^2$ Absorbance at 560 nm | Incident light intensity 223 $\mu W/cm^2$ Absorbance at 560 nm | Incident light intensity 633 $\mu W/cm^2$ Absorbance at 560 nm |
| --- | --- | --- | --- |
| 0 | 0.008 | 0.008 | 0.008 |
| 2 | 0.027 | 0.043 | 0.090 |
| 4 | 0.044 | 0.085 | 0.189 |
| 6 | 0.066 | 0.120 | 0.299 |
| 8 | 0.088 | 0.152 | 0.417 |
| 10 | 0.112 | 0.192 | 0.533 |
| 12 | 0.135 | 0.214 | 0.645 |
| 14 | 0.160 | 0.234 | 0.738 |
| 16 | 0.184 | 0.257 | 0.816 |
| Δ absorbance in 16 min | 0.176 | 0.249 | 0.808 |
| Superoxide Anion μM in 16 min | 46.9 | 66.4 | 215.4 |
| Superoxide Anion μM/min | 2.93 | 4.15 | 13.46 |
| μM Superoxide Anion min/μW/cm² | 0.029 | 0.018 | 0.021 |

Results
The irradiation of the solution comprising the reference sample with riboflavin phosphate and NBT causes appreciable change of the absorption. This trend is confirmed at different light intensities and is proportional in the solution irradiated at higher power.

1. The irradiated reference sample produces ROS, the superoxide anion production in 16 minutes determines a considerable change of absorbance;
2. The ROS production is proportional to the incident light intensity and increases with increasing of light power.
3. The ROS production expressed as amount of anion superoxide per minute and per irradiation intensity unit ($\mu W/cm^2$) is quite similar at the three light intensity applied, hence, in the experiment carried out concentrations of riboflavin phosphate and NET are in the right ratio.

The result is graphically shown in FIG. 1.

Ability of Producing ROS by Composition Comprising Inclusion Complex of Riboflavin and HP-β-Cyclodextrin—Comparison with Composition Comprising Riboflavin Phosphate.

In order to compare the ability to produce ROS the following composition were prepared:

A. In Phosphate Buffer

| Sample 1 | |
|---|---|
| Ingredients | % w/w |
| Riboflavin sodium 5'monophosphate•2H$_2$O | 0.147 |
| Na$_2$HPO$_4$•2H$_2$O | 0.067 |
| NaH$_2$PO$_4$•2H$_2$O | 0.285 |
| Distilled water | Up to 100 g |
| pH | 7.2 |

| Sample 2 | |
|---|---|
| Ingredients | % w/w |
| Complex Riboflavin-HP-β-cyclodextrin | 2.7 |
| corresponding to Riboflavin | 0.1 |
| Na$_2$HPO$_4$•2H$_2$O | 0.067 |
| NaH$_2$PO$_4$•2H$_2$O | 0.285 |
| Distilled water | Up to 100 g |
| pH | 7.2 |

Figure 2:
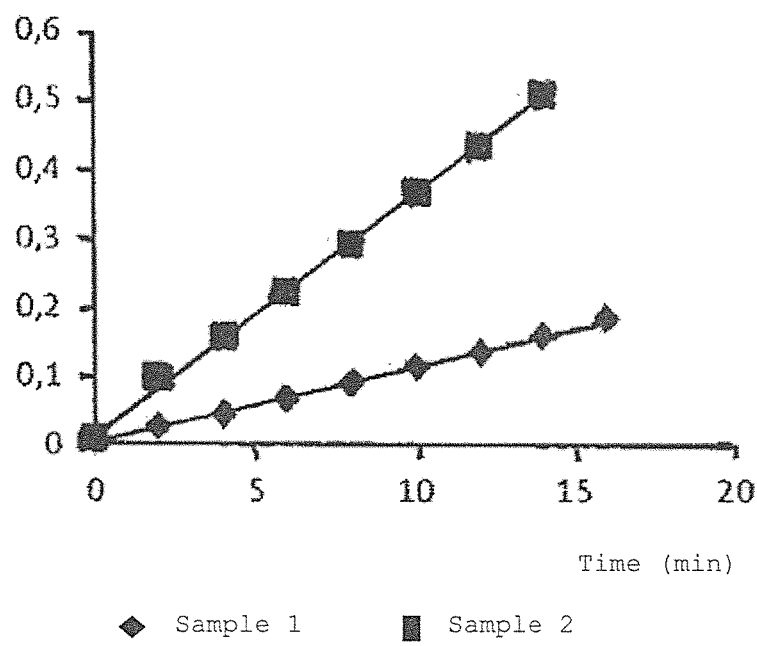
FIG. 2 is the graph showing the variation of the absorbance at 560 nm of the riboflavin sodium 5'monophosphate.2H$_2$O solution (sample 1) and the complex of riboflavin-hydroxypropyl-β-cyclodextrin (sample 2) when irradiated by 99 μW/cm$^2$ incident light.

The two samples were irradiated in the photoactivation chamber by 99 μW/cm$^2$ incident light, and absorbance at 560 nm was recorded according to the above described procedure. Relative absorbance measurement results are shown in table 8: Graphic representation is given in FIG. 2.

TABLE 8

| Comparison of absorbance in presence of phosphate buffer | | |
|---|---|---|
| Time min | Sample 1 | Sample 2 |
| 0 | 0.008 | 0.008 |
| 2 | 0.027 | 0.096 |
| 4 | 0.044 | 0.156 |
| 6 | 0.066 | 0.222 |
| 8 | 0.088 | 0.291 |
| 10 | 0.112 | 0.365 |
| 12 | 0.135 | 0.434 |
| 14 | 0.160 | 0.507 |
| 16 | 0.184 | 0.674 |
| Superoxide Anion μM in 16 min | 48.96 | 179.68 |
| Superoxide Anion μM/min | 3.06 | 11.23 |
| μM Superoxide Anion min/μW/cm$^2$ | 0.0309 | 0.133 |

Results

The comparison between sample 1 and sample 2 shows that in phosphate buffer sample 2 comprising riboflavin included in cyclodextrins produces an amount of superoxide anion exceeding 3.68 fold the amount of superoxide anion produced by the sample 1 comprising riboflavin phosphate.

The result demonstrates that riboflavin complexed in cyclodextrins not only has the ability to produce superoxide anion, but such ability is significantly higher than that riboflavin phosphate equimolar ratio has.

Noteworthy, the two compositions comprise equimolar amount of riboflavin, hence any difference in superoxide anion, production is due to a different reactivity related to different technical features of the two composition.

B. In Presence of EDTA H4 0.1% w/w—Tromethamine 0.134% w/w.

| Sample 3 | |
|---|---|
| Ingredients | % w/w |
| Riboflavin sodium 5' monophosphate•2H$_2$O | 0.147 |
| EDTA H4 | 0.1 |
| Tromethamine | 0.135 |
| Distilled water | Up to 100 g |

| Sample 4 | |
|---|---|
| Ingredients | % w/w |
| Complex Riboflavin-HP-β-cyclodextrin | 2.7 |
| corresponding to Riboflavin | 0.1 |
| EDTA H4 | 0.1 |
| Tromethamine | 0.135 |
| Distilled water | Up to 100 g |

Figure 3:
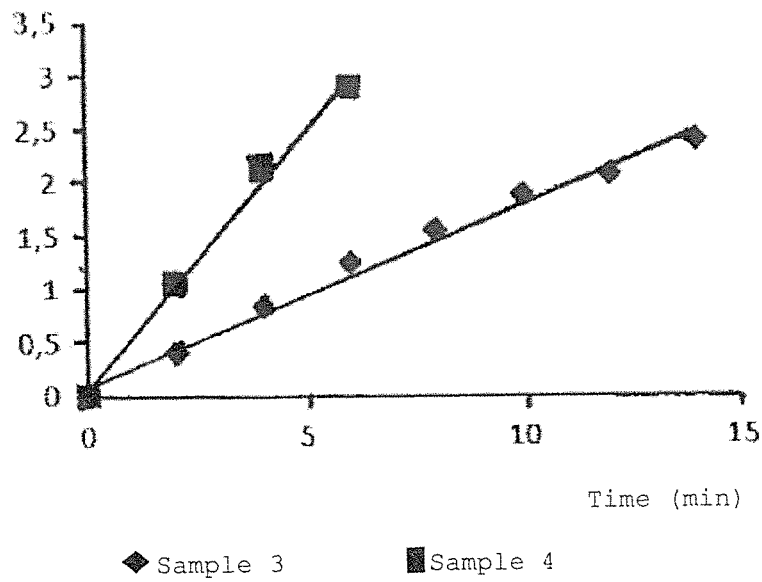
FIG. 3 is the graph showing the variation of the absorbance at 560 nm of the riboflavin sodium 5'monophosphate.2H$_2$O solution in presence of EDTA H$_4$ 0.100% w/v and tromethamine 0.135% (sample 3) and the complex of riboflavin-hydroxypropyl-β-cyclodextrin (sample 4) in presence of EDTA H$_4$ 0.100% w/v and tromethamine 0.135% when irradiated by 99 μW/cm$^2$ incident light.

The two samples were irradiated in the photoactivation chamber by 99 μW/cm$^2$ incident light and 366 nm wavelength, and absorbance at 560 nm was recorded according to the above described procedure. Relative absorbance measurement results are shown in table 9: Graphic representation is given in FIG. 3.

TABLE 9

| Comparison of absorbance in presence of EDTA H4 0.1% w/w/tromethamine 0.134% w/w | | |
|---|---|---|
| Time min | Sample 3 | Sample 4 |
| 0 | 0.008 | 0.008 |
| 2 | 0.404 | 1.060 |
| 4 | 0.841 | 2.149 |
| 6 | 1.253 | 2.895 |
| 8 | 1.549 | out of range |
| 10 | 2.065 | out of range |
| 12 | 2.389 | out of range |
| 14 | 2.689 | out of range |
| 16 | 0.184 | out of range |
| Superoxide Anion μM in 16 min | 717066 | 772000 |
| Superoxide Anion μM/min | 44816 | 128667 |
| μM Superoxide Anion min/μW/cm$^2$ | 0.450 | 1.299 |

Results

The comparison between sample 3 and sample 4 shows that in presence of 0.1% EDTA and 0.135% tromethamine (w/w) sample 4 comprising riboflavin included in cyclodextrins produces 2.87 fold the amount of superoxide anion than sample 3 comprising equimolar ration of non-complexed riboflavin phosphate.

The result demonstrates that riboflavin complexed in cyclodextrins not only has the ability to produce superoxide anion (as already proved at point A in phosphate buffer), but such ability is significantly higher than that exerted by sample 2.

Noteworthy, in sample 2 and 4 riboflavin Content is the same; the two samples differ in the presence of phosphate buffer (sample 2) and EDTA—tromethamine (sample 4), hence, EDTAH4 and tromethamine presence enhances more than $11 \cdot 10^4$ fold the ability of complexed riboflavin to produce ROS. Furthermore, the presence of phosphate buffer in the composition decreases the capacity to produce superoxide anions.

C. In Presence of EDTA H4 0.2% w/w—Tromethamine 0.235% w/w.

| Sample 5 | |
| --- | --- |
| Ingredients | % w/w |
| Riboflavin sodium 5'monophosphate•2H$_2$O | 0.147 |
| EDTA H4 | 0.2 |
| Tromethamine | 0.235 |
| Distilled water | Up to 100 g |

| Sample 6 | |
| --- | --- |
| Ingredients | % w/w |
| Complex Riboflavin-HP-β-cyclodextrin corresponding to Riboflavin | 2.7 0.1 |
| EDTA H4 | 0.2 |
| Tromethamine | 0.235 |
| Distilled water | Up to 100 g |

Figure 4:
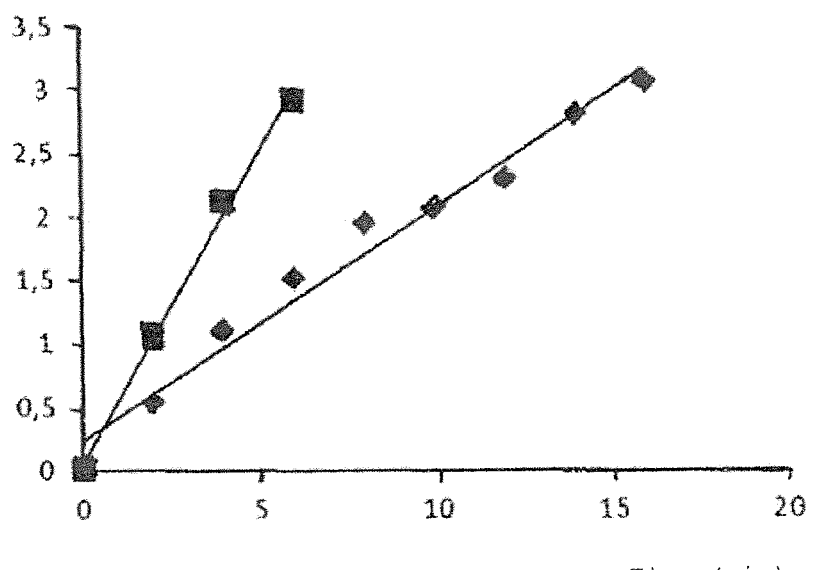
FIG. 4 is the graph showing the variation of the absorbance at 560 nm of the riboflavin sodium 5'monophosphate.2H$_2$O solution in presence of EDTA H$_4$ 0.200% w/v and tromethamine 0.235% w/v (sample 5) and the complex of riboflavin-hydroxypropyl-β-cyclodextrin (sample 6) in presence of EDTA H$_4$ 0.200% w/v and tromethamine 0.235% w/v when irradiated by 633 μW/cm$^2$ incident light.

The two samples were irradiated in the photoactivation chamber by 99 μW/cm$^2$ incident light at 366 nm wavelength, and absorbance at 560 nm was recorded according to the above described procedure. Relative absorbance measurement results are shown in table 10: Graphic representation is given in FIG. 4.

TABLE 10

Comparison of absorbance in presence of EDTA H4 0.2% w/w/tromethamine 0.235% w/w

| Time min | Sample 5 | Sample 6 |
| --- | --- | --- |
| 0 | 0.008 | 0.008 |
| 2 | 0.544 | 1.072 |
| 4 | 1.109 | 2.125 |
| 6 | 1.511 | 2.900 |
| 8 | 1.945 | out of range |
| 10 | 2.080 | out of range |
| 12 | 2.305 | out of range |
| 14 | 2.800 | out of range |
| 16 | 3.051 | out of range |
| Superoxide Anion μM in 16 min | 813600 | 773328 |
| Superoxide Anion μM/min | 50850 | 128888 |
| μM Superoxide Anion min/μW/cm$^2$ | 0.514 | 1.302 |

Results

The comparison between sample 5 and sample 6 shows that in presence of 0.2% EDTA and 0.235% tromethamine (w/w) sample 6 comprising riboflavin included in cyclodextrins produces 2.53 fold the amount of superoxide anion than sample 5 comprising non-complexed riboflavin phosphate.

Figure 5:
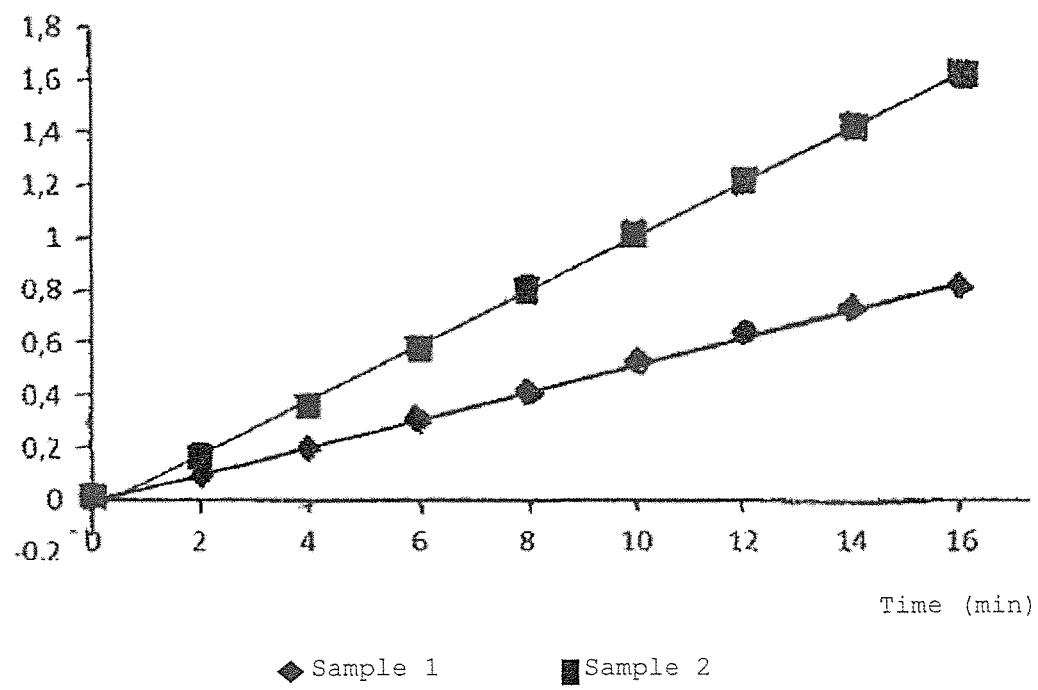
FIG. 5 is the graph showing the variation of the absorbance at 560 nm of the riboflavin sodium 5'monophosphate.2H$_2$O solution (sample 1) and the complex of riboflavin-hydroxypropyl-β-cyclodextrin (sample 2) when irradiated by 99 μW/cm$^2$ incident light.
Figure 6:
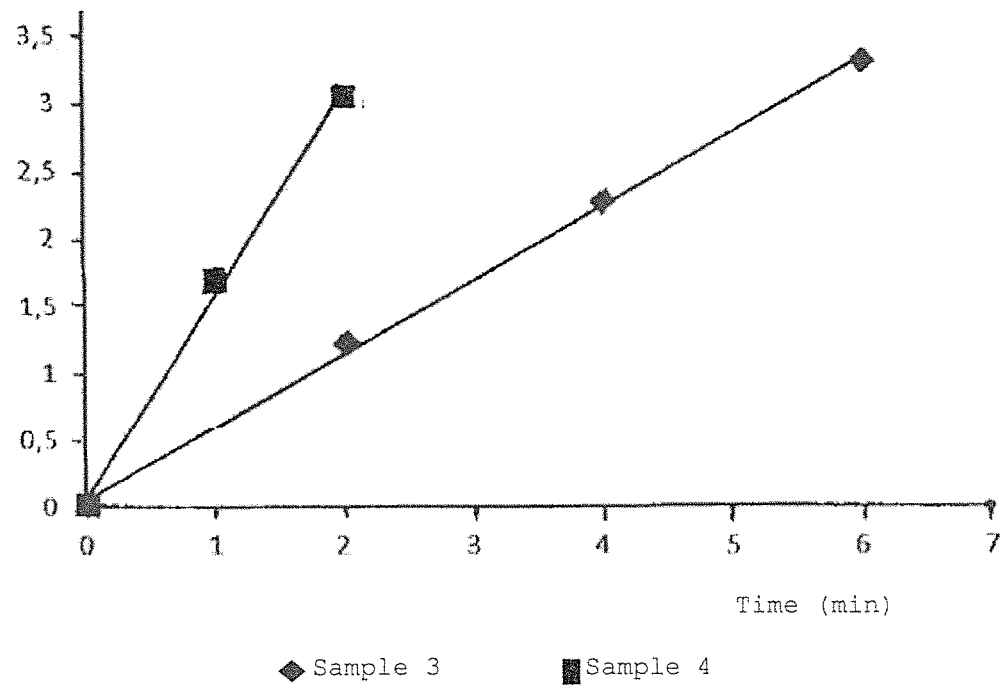
FIG. 6 is the graph showing the variation of the absorbance at 560 nm of the riboflavin sodium 5'monophosphate.2H$_2$O solution in presence of EDTA H$_4$ 0.100% w/v and tromethamine 0.135% (sample 3) and the complex of riboflavin-hydroxypropyl-β-cyclodextrin (sample 4) in presence of EDTA H$_4$ 0.100% w/v and tromethamine 0.135% w/v when irradiated by 633 μW/cm$^2$ incident light.
Figure 7:
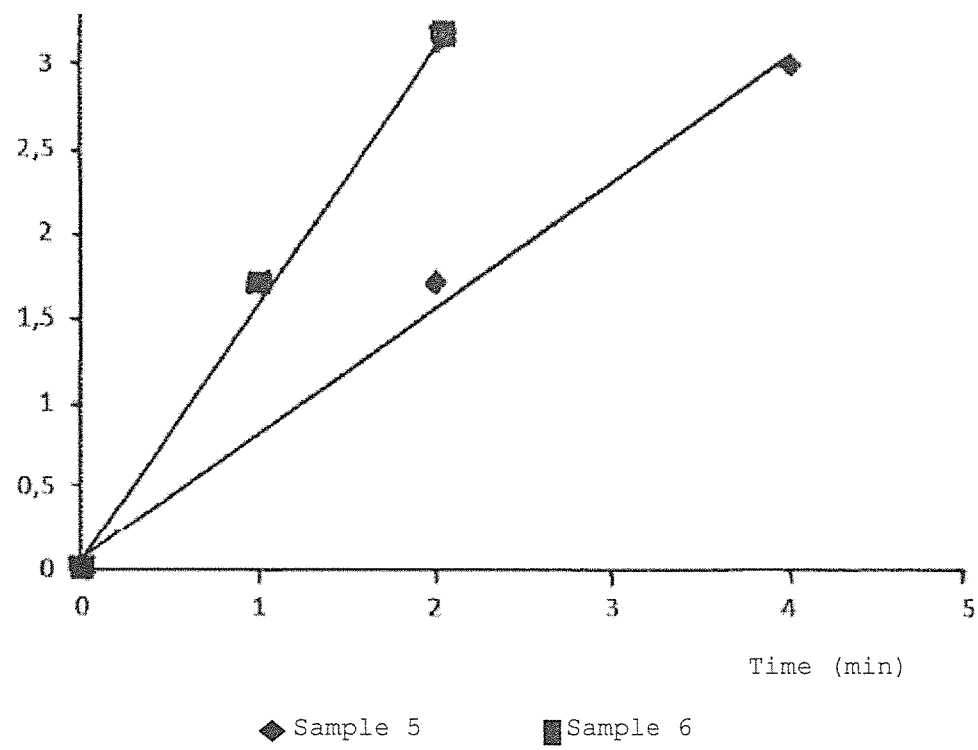
FIG. 7 is the graph showing the variation of the absorbance at 560 nm of the riboflavin sodium 5'monophosphate.2H$_2$O solution in presence of EDTA H$_4$ 0.200% w/v and tromethamine 0.235% w/v (sample 5) and the complex of riboflavin-hydroxypropyl-β-cyclodextrin (sample 6) in presence of EDTA H$_4$ 0.200% w/v and tromethamine 0.235% w/v when irradiated by 633 μW/cm$^2$ incident light. riboflavin-hydroxypropyl-β-cyclodextrin produces more superoxide than riboflavin phosphate equimolar ratio

The experiment described at point A-C has been repeated using photoactivation at 633 μW/cm$^2$ incident light intensity. Absorbance measurements results are reported in table 11-13 and graphically shown in FIGS. 5-7.

TABLE 11

Comparison of absorbance in presence of phosphate buffer

| Time min | Sample 1 | Sample 2 |
| --- | --- | --- |
| 0 | 0.008 | 0.008 |
| 2 | 0.090 | 0.167 |
| 4 | 0.189 | 0.364 |
| 6 | 0.299 | 0.575 |
| 8 | 0.417 | 0.797 |
| 10 | 0.533 | 1.010 |
| 12 | 0.645 | 1.215 |
| 14 | 0.738 | 1.426 |
| 16 | 0.816 | 1.630 |
| Superoxide Anion μM in 16 min | 217.6 | 434.7 |
| Superoxide Anion μM/min | 13.6 | 27.2 |
| μM Superoxide Anion min/μW/cm$^2$ | 0.0215 | 0.0429 |

TABLE 12

Comparison of absorbance in presence of EDTA H4 0.1% w/w/tromethamine 0.135% w/w

| Time min | Sample 3 | Sample 4 |
| --- | --- | --- |
| 0 | 0.008 | 0.008 |
| 2 | 1.217 | 3.046 |
| 4 | 2.255 | out of range |
| 6 | 3.306 | out of range |
| 8 | out of range | out of range |
| 10 | out of range | out of range |
| 12 | out of range | out of range |
| 14 | out of range | out of range |
| 16 | out of range | out of range |
| Superoxide Anion μM at end of reaction | 881.6 | 812.3 |
| Superoxide Anion μM/min | 146.9 | 406.1 |
| μM Superoxide Anion min/μW/cm$^2$ | 0.232 | 0.641 |

TABLE 13

Comparison of absorbance in presence of EDTA H4 0.2% w/w/tromethamine 0.235% w/w

| Time min | Sample 3 | Sample 4 |
| --- | --- | --- |
| 0 | 0.008 | 0.008 |
| 2 | 1.710 | 3.068 |
| 4 | 3.004 | out of range |
| 6 | out of range | out of range |
| 8 | out of range | out of range |
| 10 | out of range | out of range |
| 12 | out of range | out of range |
| 14 | out of range | out of range |
| 16 | out of range | out of range |
| Superoxide Anion μM at end of reaction | 801.1 | 818.1 |
| Superoxide Anion μM/min | 133.5 | 409.1 |
| μM Superoxide Anion min/μW/cm$^2$ | 0.210 | 0.646 |

Results

The experiment has shown that also following photoactivation by 633 μW/cm$^2$ incident light intensity sample comprising riboflavin included in cyclodextrins produces superoxide anion in higher amount than sample comprising riboflavin phosphate, however the intensity of the incident light is so high that reaction has to be stopped after 4-6 minutes.

In conclusions, a complex of riboflavin included in HP β-CD when irradiated by whatever light intensity (99, 223, 669 μW/cm$^2$), both in presence or without EDTA, produces more superoxide anion than equimolar riboflavin phosphate solution irradiated at same light intensity without or in presence EDTA.

STUDY 3—Determination of Permeation Ability Ex-Vivo in Rabbit Eye. Comparison of Riboflavin/HP-β-Cyclodextrin Complex Versus Riboflavin/β-Cyclodextrin Complex.

For each experimental point two rabbits (New Zealand, 2-2.5 kg, male, 9 weeks) (four eyes) were used. The rabbit was anesthetized by intramuscular injection of a mixture of tiletamine hydrochloride and zolazepam hydrochloride (Zoletil 100®, Virbac, Milan); then the rabbit was sacrificed by intravenous administration of 0.3 ml/kg of Tanax® (Intervet Italy, Milan).

The eye enucleating was performed immediately after the sacrifice; explanted eyes were placed vertically on a suitable support; on the surface of the eye a "corneal silicone ring" acting as a reservoir of the tested riboflavin formulations was placed. In such reservoir 1 ml of the riboflavin formulation to be tested is added.

In order to identify the optimal parameters of the formulations having the required technical features able to determine the better riboflavin permeation of the cornea several experiments have been performed. As control the riboflavin permeation obtained with a riboflavin solution, indicated as C, (riboflavin phosphate dehydrated sodium salt 0.0147% w/w, sodium EDTA 0.1% w/w, tromethamine 0.05% w/w) instilled in the eyes for 15 minutes followed by, UV-A irradiation for 5 minutes and corneal epithelium removal (so called Epi off procedure) as described in WO 2010/023705.

The explanted corneas are stored at −20° C. before to proceed with the quantitative analysis by HPLC/MS-MS.

At the time of the quantitative analysis rabbit corneas were thawed, weighed, chopped and homogenized on ice by Ultra-TURRAX® and then sonicated in a solution of Acetonitrile: bidistilled Water (50:50) to extract the riboflavin, and finally centrifuged for 15 min at 10,000 rpm and at a temperature of 4° C.

HPLC/MS-MS analysis was performed by the Agilent 1100 Series HPLC system coupled to a 6410 of Agilent triple quadrupole mass spectrometer.

HPLC Parameters are Reported Below

| Item | Description |
| --- | --- |
| Analytical column | Phenomenex, Kinetex, 4.6 × 50 mm, 2.6 μm, C8 HILIC |
| Pre-column | Phenomenex, Gemini-NX, 4 × 2.0 mm |
| Column oven temperature | 25° C. |
| HPLC Solution (A) | 100 mM Ammonium formate buffer solution pH 3.2 |
| HPLC Solution (B) | Acetonitrile |
| Mobile phase composition | A = 10% B = 90% |
| Flow rate | 0.1 mL/min |
| Autosampler temperature | +4° C. |
| Injection volume | 20 μL |
| Retention times | About 0.5 minutes |
| Total run time | 3 minutes |

Mass Spectrometry

A. Detection is in the positive ion mode using a API/ESI interface and Multiple Reaction Monitoring (MRM)
Mass transitions: 377→243 m/z for riboflavin
B. Operating conditions and MS parameters are reported below:

| MS Parameters | |
| --- | --- |
| Gas Temperature | 350° C. |
| Gas Flow | 6 l/min |
| Nebulizer | 30 psi |
| Capillary | 3500 V |
| Collision energy | 30 V |
| Dwell-time | 200 msec |
| Fragmentor | 160 |

The carried out experiments and the relative tested riboflavin formulations are reported below.

Experiment 1—Corneal Absorption of Riboflavin/β-Cyclodextrin Complex

Figure 8:
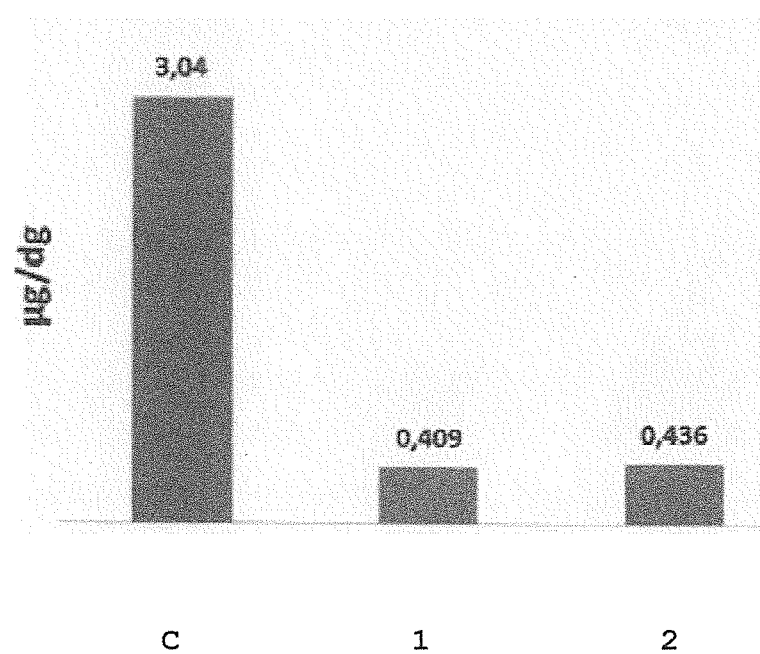
FIG. 8 is the graph showing the riboflavin permeation into rabbit corneas of riboflavin/β-cyclodextrin complexes comprising different amount of riboflavin and β-cyclodextrin, respectively, (1) 0.1% w/w riboflavin and 2.6% w/w β-cyclodextrin, (2) 0.1% w/w riboflavin and 1.3% w/w β-cyclodextrin, (3) 0.05% w/w riboflavin and 1.3% w/w β-cyclodextrin, compared to the corneal permeation following the classical corneal cross-linking treatment with riboflavin phosphate dehydrated sodium salt 0.0147% w/w, sodium EDTA 0.1% w/w, tromethamine 0.05% w/w solution instilled in the eyes for 15 minutes followed by UV-A irradiation for 5 minutes and corneal epithelium removal.

C—riboflavin phosphate dehydrated sodium salt 0.0147% w/w, sodium EDTA 0.1% w/w, tromethamine 0.05% w/w, instilled in the eyes for 15 minutes followed by UV-A irradiation for 5 minutes and corneal epithelium removal;

1—riboflavin/β-cyclodextrin complex (0.1% w/v riboflavin 2.6% β-cyclodextrin) in 0.1% w/v EDTA, 0.05% w/v tromethamine (such composition is not soluble, the complex precipitates);

2—riboflavin/β-cyclodextrin complex (0.1% w/v riboflavin 1.3% β-cyclodextrin) in 0.1% w/v EDTA, 0.05% w/v tromethamine (such composition remains in solution for a short time, afterward the complex precipitates);

3—riboflavin/β-cyclodextrin complex (0.05% w/v riboflavin 1.3% β-cyclodextrin) in 0.1% w/v EDTA, 0.05% w/v tromethamine (FIG. 8).

Experiment 2—Corneal Absorption of Riboflavin/HP-β-Cyclodextrin Complex

Figure 9:
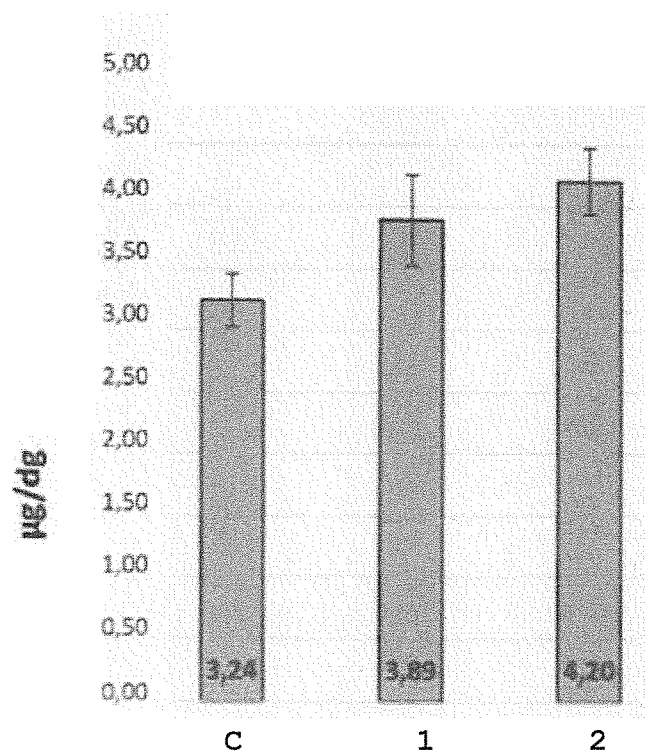
FIG. 9 is the graph showing the effect of the sterilization (Filtration 0.22 micron, steam at 121° C. 20 mins at 1 atm) procedures on the riboflavin permeation into rabbit corneas of a riboflavin/hydroxypropil-β-cyclodextrin complex formulation compared to the corneal permeation following the classical corneal cross-linking treatment.

C—riboflavin phosphate dehydrated sodium salt 0.0147% w/w, sodium EDTA 0.1% w/w, tromethamine 0.05% w/w, instilled in the eyes for 15 minutes followed by UV-A irradiation for 5 minutes and corneal epithelium removal;

1—riboflavin/HP-β-cyclodextrin complex (0.1% w/v riboflavin, 2.6% HP-β-cyclodextrin) in 0.1% w/v EDTA H4, 0.134% w/v tromethamine, sterilized by filtration, pH 7.4;

2—riboflavin/HP-β-cyclodextrin complex (0.1% w/v riboflavin, 2.6% HP-β-cyclodextrin) in 0.1% w/v EDTA H4, 0.134% w/v tromethamine, sterilized at 121° C., pH 6.8 (FIG. 9).

Experiment 3—Corneal Absorption of Riboflavin/HP-β-Cyclodextrin Complex at Lower Concentration of HP-β-Cyclodextrin.

Figure 10:
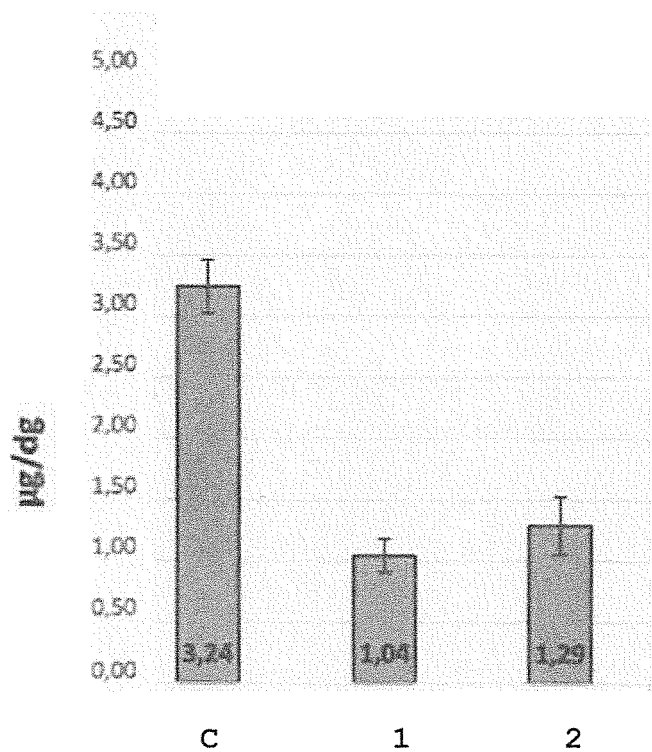
FIG. 10 is the graph showing the effect of the different amount of EDTAH$_4$ and tromethamine on the riboflavin permeation into rabbit corneas of a riboflavin/hydroxypropil-β-cyclodextrin complex formulation compared to the corneal permeation following the classical corneal cross-linking treatment.

C—riboflavin phosphate dehydrated sodium salt 0.0147% w/w, sodium EDTA 0.1% w/w, tromethamine 0.05% w/w, instilled in the eyes for 15 minutes followed by UV-A irradiation for 5 minutes and corneal epithelium removal;

1—riboflavin/HP-β-cyclodextrin complex (0.1% w/v riboflavin, 1.2% w/v HP-β-cyclodextrin) in 0.1% w/v EDTA H4, 0.134% w/v tromethamine, sterilized at 121° C., pH 7.0;

2—riboflavin/HP-β-cyclodextrin complex (0.1% w/v riboflavin, 1.2% w/v HP-β-cyclodextrin) in 0.1% w/v EDTA, 0.134% w/v tromethamine, sterilized at 121° C., pH 7.0 (FIG. 10).

Results

The determination of permeation ability ex-vivo in rabbit eye has confirmed that formulations wherein riboflavin is complexed into HP-β-cyclodextrin are more effective both in absorption ability and stability. The best result is obtained using the complex of riboflavin in HP-β-cyclodextrin complex (0.1% w/v riboflavin, 2.6% HP-β-cyclodextrin) in 0.1% w/v EDTA H4, 0.134% w/v tromethamine. Furthermore, sterilization by heating of the used composition appears to improve the composition performance in comparison to the sterilization by filtration.

CONCLUSION

The overall results from the study allow concluding that ophthalmic composition suitably developed to perform corneal cross-linking comprising riboflavin included in HP beta cyclodextrins are more effective due to its ability to produce higher amount of superoxide anion than prior art formulation comprising riboflavin phosphate. In fact, unexpectedly it has been demonstrated that phosphate buffer decreases capacity of producing superoxide anions, whereas so far it was known that the presence of phosphate could decrease the stability of riboflavin, but no hints there were about the effect on superoxide production, which is pivotal for corneal interweaving of collagen fibers in the treatment of ocular ectasia.

The technical feature of the composition according to the invention allows improving performance of prior art composition overcoming the relative drawback due to phosphate anion of riboflavin. In fact, the phosphate group of riboflavin in ophthalmic composition is necessary for the solubility of the molecule, otherwise not soluble, but it adversely affects stability and photodegradation thereof, influencing the ROS production and pathway to the corneal cross linking.

The presence of EDTA H4 notably enhances the ability to produce superoxide anion, and such effect is more marked in composition containing complexed riboflavin; moreover this capacity can be modulated by modifying EDTA and Tris concentration.

Therefore, as broadly demonstrated the inclusion complex of riboflavin in HP-β-cyclodextrin is an improved photosensitizer agent in the riboflavin-UV mediated cross-linking of corneal collage fibers and the ophthalmic compositions comprising it allow to overcome some drawbacks of the prior art compositions.

BIBLIOGRAPHY

1. Song, P. S. Chemistry of flavins in their excited states. In *Flavins and Flavoprotein*; Kamin, H., Ed.; University Park Press: Baltimore, USA, 1971; pp 37-61.
2. Ahmad I. et al. Int. J. Pharm. 2004. 280; 199-208.
3. Schuman Jorns M., et al., Eur. J. Biochem. 1975, 57, 35-48.
4. Ahmad I. et al. J. Photochem. Photobiol., B: Biol. 2008, 93, 82-87.
5. Yoshioka, S.; Stella, V. J. Stability of Drugs and Dosage Forms; Kluwer Academic/Plenum Publishers: New York, USA, 2000; pp 97-99.
6. Moore W. W., Ireton R. C. Photochem. Photobiol. 1977, 25, 347-356.
7. Koziol J. Photochem. Photobiol. 1966, 5, 55-62.
8. Asker A. F., Habib M. J. Drug Dev. Ind. Pharm. 1990, 16, 149-156.
9. Holmström B., Oster G. J. Am. Chem. Soc. 1961, 83, 1867-1871.
10. Guttman D. E. J. Pharm. Sci. 1962, 51, 1162-1166.
11. Sato Y. et al. Chem. Pharm. Bull. 1982, 30, 1803-1810.
12. Loukas, Y. L. J. Pharm. Biomed. Anal. 2001, 26, 255-263.
13. de Jesus M. B. et al. E. J. Pharm. Pharmacol. 2012, 64, 832-842.
14. Challa R. et al. AAPS PharmSciTech. 2005, 6, 329-357.
15. Grove C. et al. J. Cosmet. Sci. 2003, 54, 537-550.
16. Sultana Y. et al. Curr. Drug Delivery. 2006, 3, 207-217.
17. Roy D. K. et al. Spectrochim. Acta. 2009, 73, 201-204.
18. Terekhova I. V. et al. J. Inclusion Phenom. Macrocyclic Chem. 2011, 69, 167-172.
19. Morrison W. J. et al. Molecular pharmaceutics 2013, 10, 756-762.
20. Zaidi T. et al. Invest. Ophthalmol. Vis. Sci. 2008, 49, 1000-1009.
21. Ohtani Y. Et al. Eur. J. Biochem. 1989, 186, 17-22.

We claim:

1. A method of using a complex of riboflavin with hydroxypropylated β-cyclodextrins as photosensitizer in the riboflavin-UV mediated cross-linking of corneal collagen fibers, wherein the weight ratio of hydroxypropyl-β-cyclodextrin to riboflavin is 26, and
    wherein the method comprises administering the complex to a patient in need thereof, and wherein said riboflavin-UV mediated cross-linking is performed with ultraviolet-A (UVA) irradiation at a wavelength of 366 nm and at different incident light intensity selected from a group consisting of 99 $\mu W/cm^2$, 233 $\mu W/cm^2$, and 633 $\mu W/cm^2$.

2. The method of claim 1 wherein the complex of riboflavin with hydroxypropylated β-cyclodextrins is used for the preparation of a corneal cross-linking ophthalmic composition in the treatment of the keratoconus or of other corneal ectatic disorders in order to favor the passage of the ophthalmic composition to the corneal stroma through the corneal epithelium.

3. The method of claim 1 wherein the complex comprises 0.05% w/v of riboflavin and 1.3% w/v of hydroxypropylated β-cyclodextrins.

4. An ophthalmic composition comprising a complex of riboflavin with hydroxypropyl-β-cyclodextrin, wherein the weight ratio of hydroxypropyl-β-cyclodextrin to riboflavin is 26; Ethylene Diamine Tetraacetic Acid (EDTA H4) or a salt thereof; and tromethamine; and having pH value ranging between 6.0 and 7.3,
    wherein the complex of riboflavin with hydroxypropyl-β-cyclodextrin ranges between 2 and 3% by total weight; the EDTA H4 or a salt thereof ranges between 0.05 and 0.25% by total weight; and the tromethamine ranges between 0.12 and 0.3% by total weight.

5. The ophthalmic composition of claim 4 wherein the complex of riboflavin with hydroxypropyl-β-cyclodextrin ranges between 2.5 and 2.9% by total weight; the EDTA H4 or a salt thereof ranges between 0.08 and 0.22% by total weight; and the tromethamine ranges between 0.134 and 0.285% by total weight.

6. The ophthalmic composition of claim 4 wherein the composition comprises the following formulation:
    the complex of riboflavin with hydroxypropyl-β-cyclodextrin at 2.5-2.7% by total weight,
    the EDTA H4 at 0.1% by total weight,
    the Tromethamine at 0.130-0.150% by total weight, and
    distilled water to make 100% by total weight of the composition.

7. The ophthalmic composition of claim 4 further comprising other active principles, buffering agents, preservatives, vehicles, diluents, or pharmaceutically acceptable excipients.

8. The ophthalmic composition of claim 4 wherein the composition is in a pharmaceutical form of a collyrium, an eye-drop, an eye-wash, an ointment, or other pharmaceutical forms.

9. An ophthalmic composition comprising a complex of riboflavin with hydroxypropyl-β-cyclodextrin, wherein the weight ratio of hydroxypropyl-β-cyclodextrin to riboflavin is 26; Ethylene Diamine Tetraacetic Acid (EDTA H4) or a salt thereof; and tromethamine; and having pH value ranging between 6.0 and 7.3; wherein the ophthalmic composition is used in the treatment of the keratoconus or of other corneal ectatic disorders by corneal cross-linking in order to favor the passage of the ophthalmic composition to the corneal stroma through the corneal epithelium.

* * * * *